United States Patent
Li et al.

(10) Patent No.: US 9,629,841 B2
(45) Date of Patent: Apr. 25, 2017

(54) FORMULATIONS OF PYRIMIDINEDIONE DERIVATIVE COMPOUNDS

(71) Applicant: AbbVie Inc., North Chicago, IL (US)

(72) Inventors: Yanxia Li, Libertyville, IL (US); Ping Gao, Highland Park, IL (US); Yi Shi, Libertyville, IL (US); Geoff G. Zhang, Vernon Hills, IL (US); Yi Goa, Vernon Hills, IL (US); Jianwei Wu, Potomac, MD (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/058,071

(22) Filed: Oct. 18, 2013

(65) Prior Publication Data

US 2014/0113921 A1 Apr. 24, 2014

Related U.S. Application Data

(60) Provisional application No. 61/715,766, filed on Oct. 18, 2012.

(51) Int. Cl.
| | | |
|---|---|---|
| A01N 43/54 | (2006.01) | |
| A61K 31/505 | (2006.01) | |
| A61K 31/513 | (2006.01) | |
| A61K 9/20 | (2006.01) | |
| A61K 9/28 | (2006.01) | |

(52) U.S. Cl.
CPC .......... *A61K 31/513* (2013.01); *A61K 9/2027* (2013.01); *A61K 9/2054* (2013.01); *A61K 9/2846* (2013.01); *A61K 9/2866* (2013.01)

(58) Field of Classification Search
CPC .... A61K 31/513; A61K 45/06; A61K 9/2027; A61K 9/2054; A61K 9/2846; A61K 9/2866
See application file for complete search history.

(56) References Cited

U.S. PATENT DOCUMENTS

| | | |
|---|---|---|
| 7,108,864 B1 | 9/2006 | Martino et al. |
| 8,202,912 B2 | 6/2012 | Curatolo et al. |
| 2010/0166861 A1* | 7/2010 | Lynch .................. A61K 9/2027 424/480 |

FOREIGN PATENT DOCUMENTS

| | | |
|---|---|---|
| DE | 4442257 A1 | 5/1996 |
| EP | 2583680 A2 | 4/2013 |
| WO | 2009039127 A1 | 3/2009 |
| WO | 2009039134 A1 | 3/2009 |
| WO | WO 2009039127 A1 * | 3/2009 |
| WO | 2011109274 A1 | 9/2011 |

OTHER PUBLICATIONS

Buhler, Polyvinylpyrrolidone-Excipients for Pharmaceuticals, 2005.*
DiscovIR-LC, Application Note 031, Jul. 2009.*
Jagdale et al, Rev Ciênc Farm Básica Apl., 2010;31(1):25-31.*
Alonzo D.E., et al., "Understanding the Behavior of Amorphous Pharmaceutical Systems During Dissolution," Pharmaceutical Research, 2010, vol. 27 (4), pp. 608-618.
International Search Report and Written Opinion for Application No. PCT/US2013/065760, mailed on Dec. 12, 2013, 13 pages.
Reintjes T., "Solubility Enhancement with BASF Pharma Polymers Solubilizer Compendium", [retrieved on Oct. 1, 2011]. Retrieved from the Internet: < URL: http://www.pharma-ingredients.basf.com/Documents/ENP/Brochure/EN/b_03_110921e_Solubility_Enhance_Compendium.pdf.
Sree Giri P.B., et al: "Formulation and Evaluation of Oro Dispersible Tablets of Stavudine by Direct Compression Technique", [retrived on Jan. 1, 2012], pp. 1505-1514, Retrieved from the Internet: < URL: http://scholarsresearchlibrary.com/dpl-vol4-iss5/DPL-2912-4-5-1595-1514.pdf.

* cited by examiner

*Primary Examiner* — Jean Cornet

(57) ABSTRACT

The present disclosure relates to pharmaceutical compositions of pyrimidinedione derivative compounds and methods of preparing and uses thereof. The disclosure also relates to methods of enhancing bioavailability of pyrimidinedione derivative compounds in pharmaceutical compositions administered to a subject and methods of reducing the amount of a pyrimidinedione derivative compound in a pharmaceutical composition while achieving the same bioavailability in a subject.

32 Claims, 19 Drawing Sheets

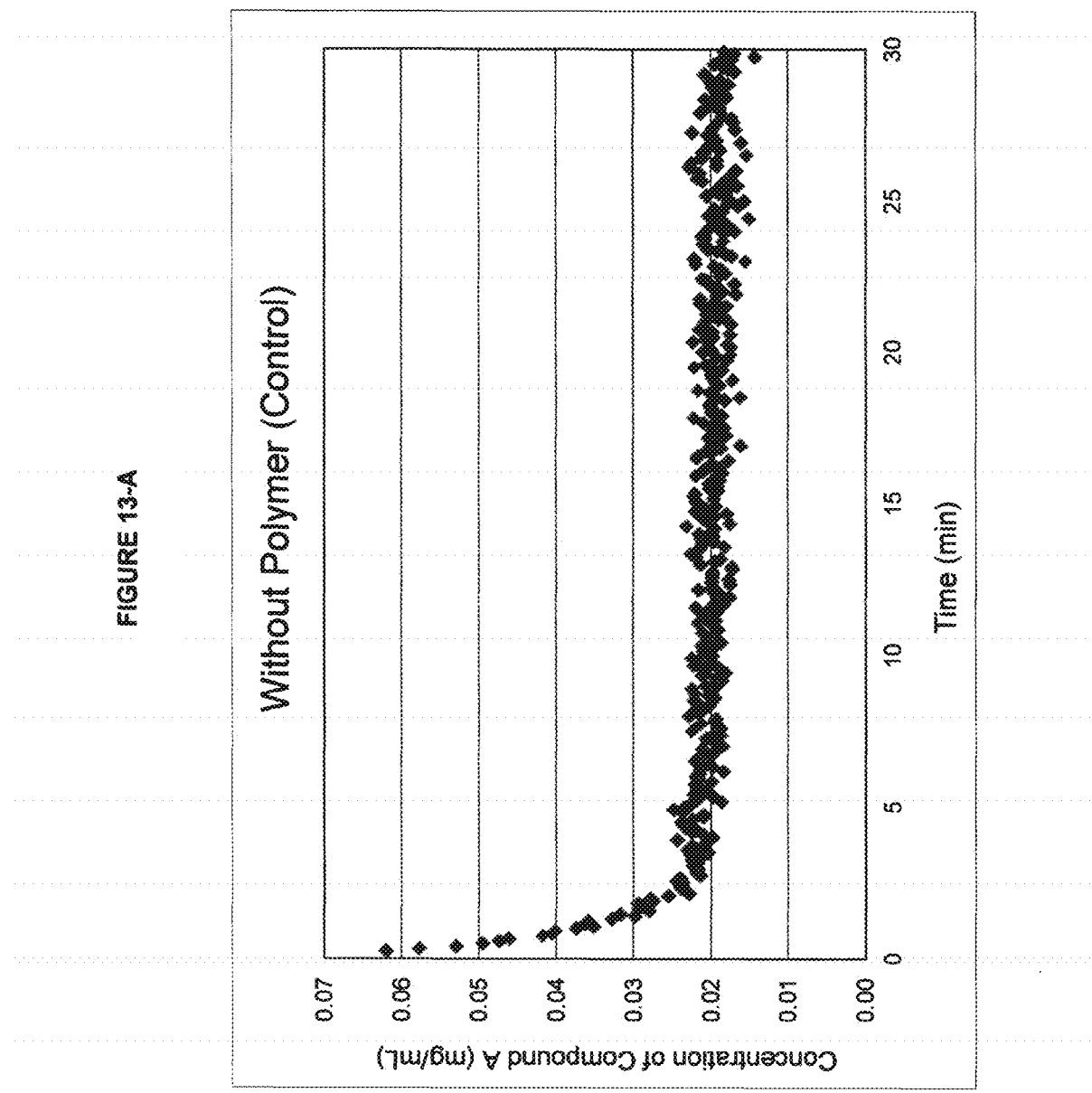

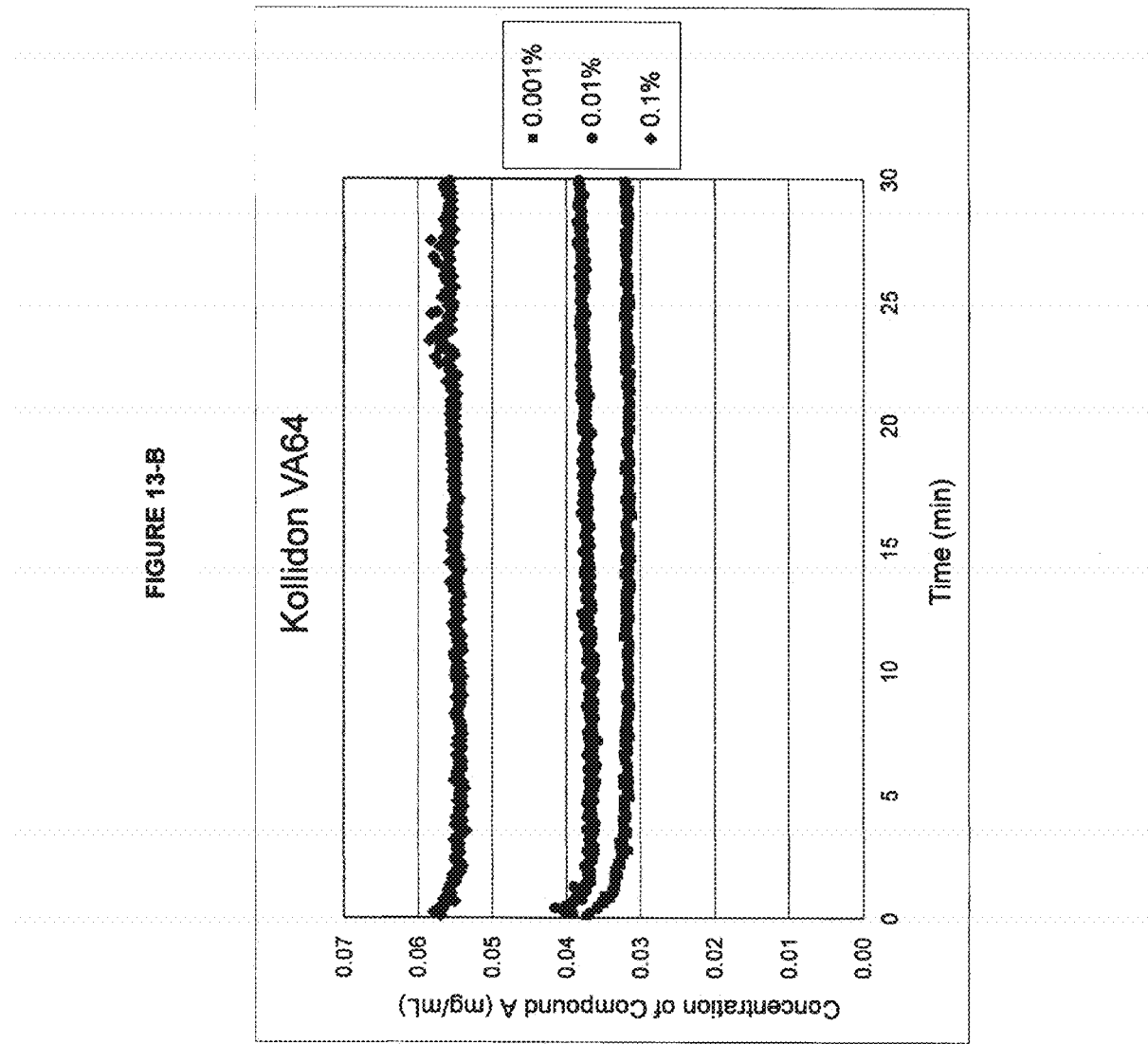

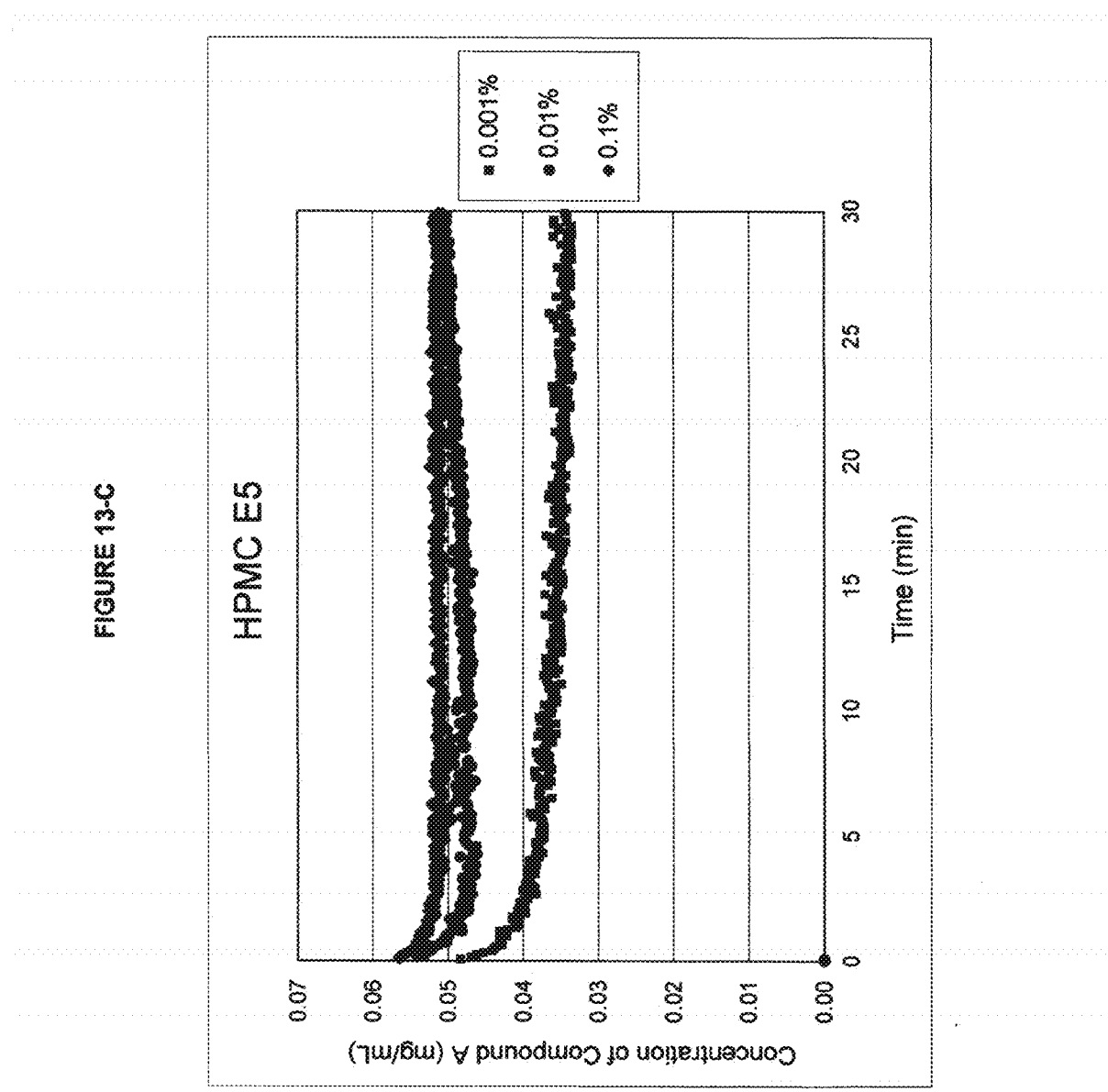
FIGURE 13-C

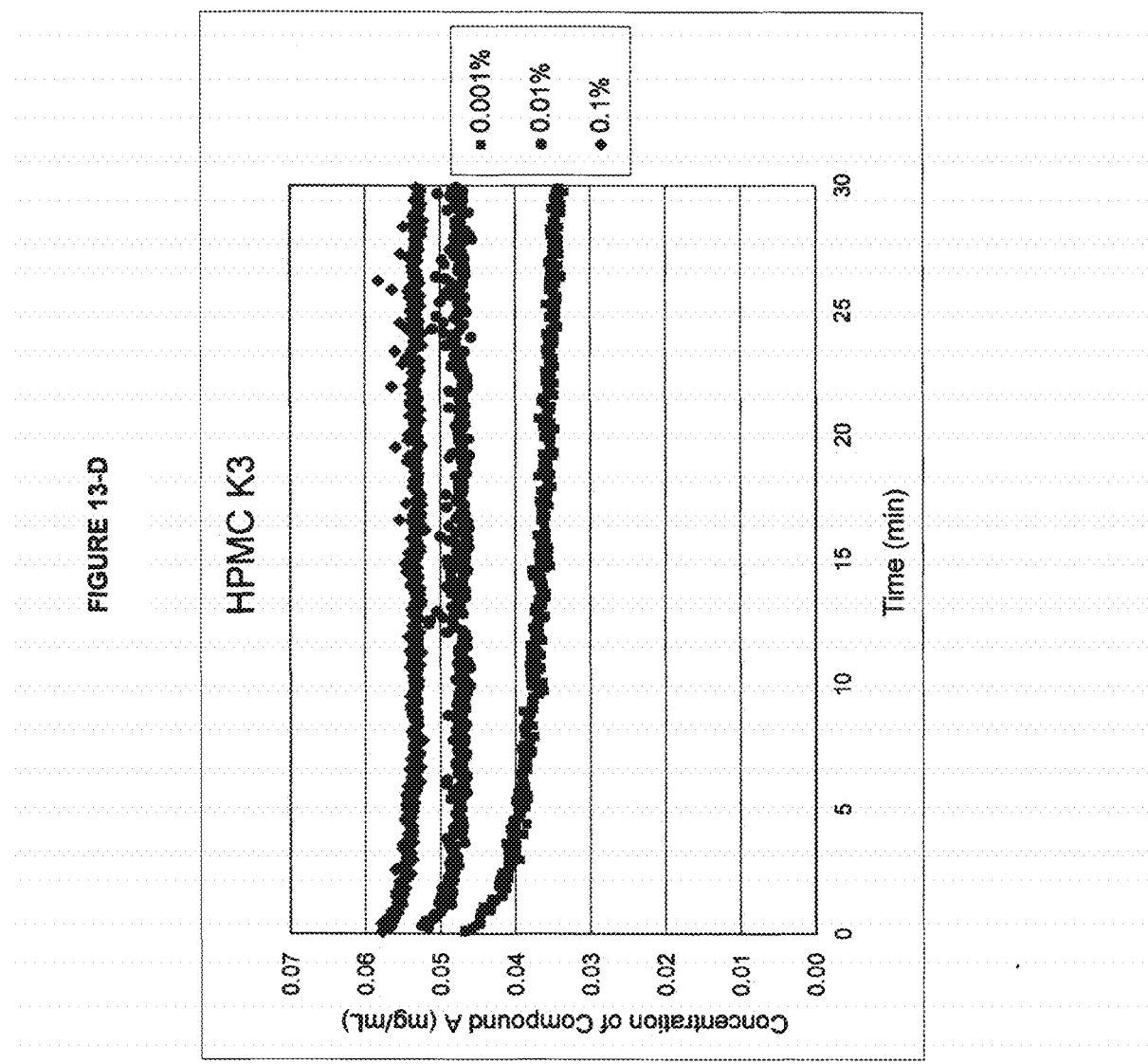

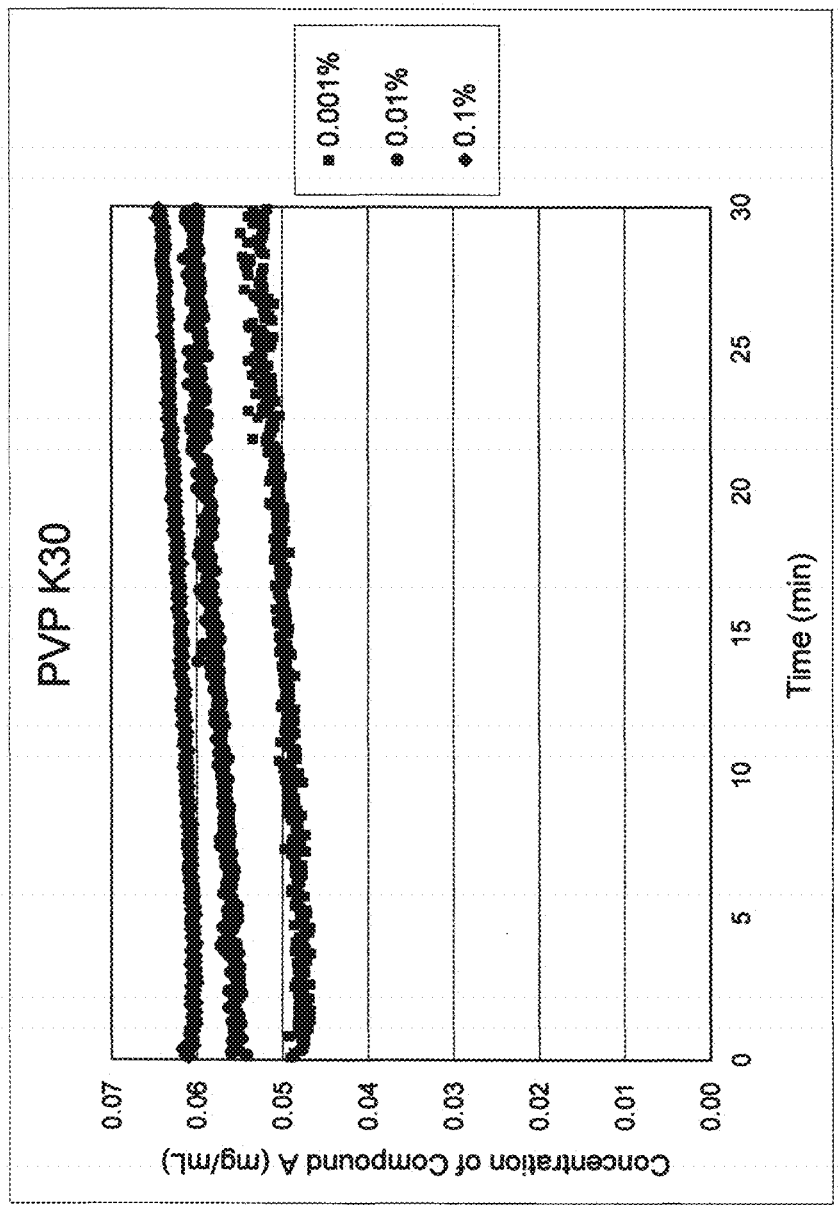

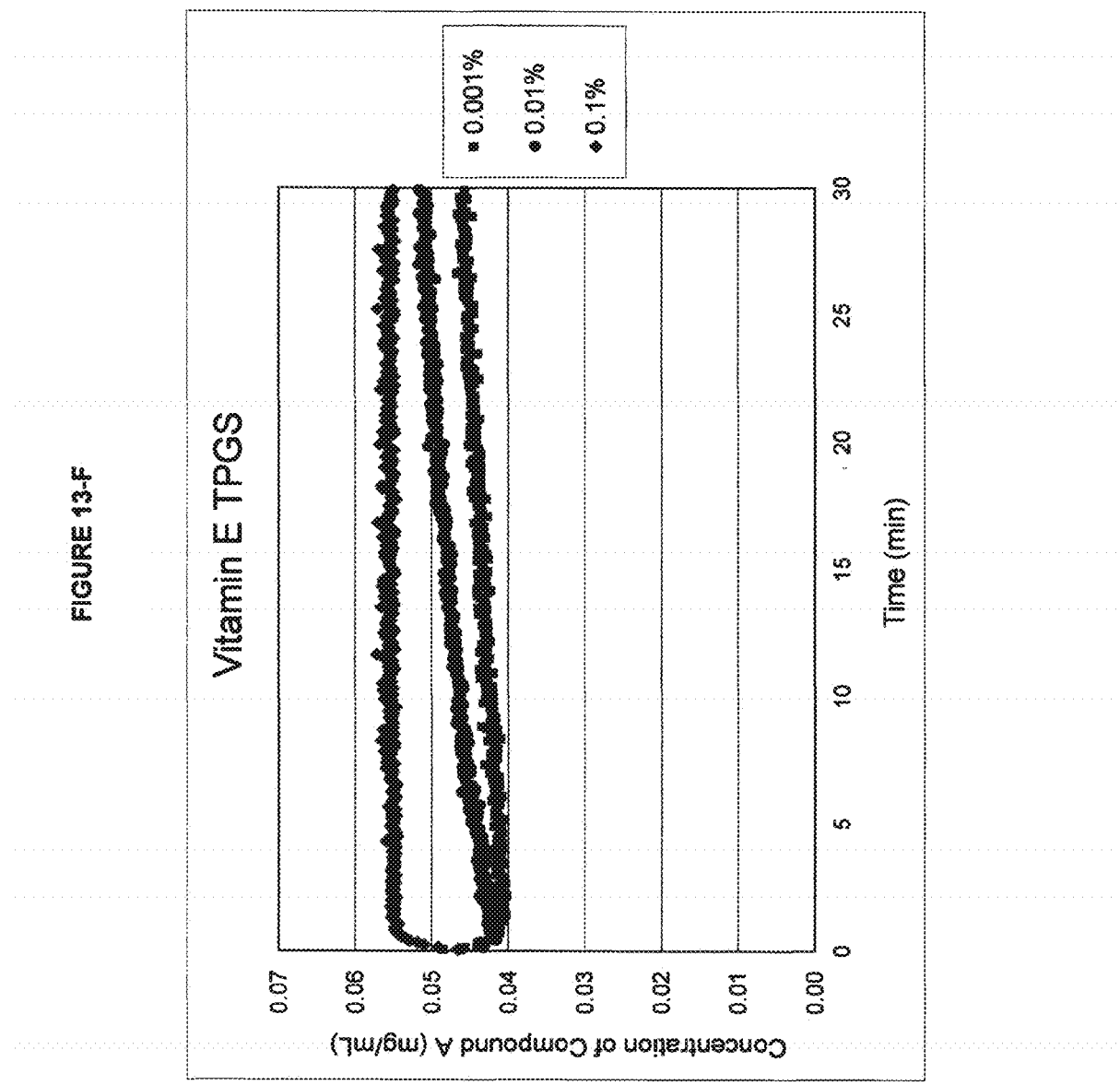

FORMULATIONS OF PYRIMIDINEDIONE DERIVATIVE COMPOUNDS

CROSS-REFERENCE TO RELATED APPLICATION

This application claims priority to U.S. Provisional Application Ser. No. 61/715,766 filed on Oct. 18, 2012. The entire text of that provisional application is incorporated by reference into this application.

TECHNICAL FIELD

This disclosure is directed to pharmaceutical compositions and methods of use of such compositions.

BACKGROUND

Pyrimidinedione derivatives are BCS II type drugs possessing low solubility and high permeability. One of the common problems of poorly water-soluble drugs is that they provide low bioavailability and/or higher variability in bioavailability resulting from poor water solubility and low dissolution.

Formation of a soluble salt form for an insoluble compound is often a means to increase drug solubility in an aqueous medium, and hence improve dissolution rate and ultimately enhance bioavailability. In some cases, however, such soluble salt may also have high bio-variability or in worst case scenario, the bioavailability of the drug is not improved at all. However, salt forms of pyrimidinedione derivative are prone to converting back to a free acid form, especially in the acidic environment of the stomach, forming a precipitate that cannot be readily absorbed. Upon exposure to an aqueous medium, the salt undergoes a dissolution process which includes dissolving of the solid particle followed by diffusion of the dissolved drug. The latter is often controlled by a diffusion layer environment. Within the diffusion layer, the salt might be dissociated to a non-ionized form which may achieve supersaturation and then precipitate out either on the exterior surface of the salt particle or in the bulk medium, preventing further dissolution of the salt, and therefore resulting in low bioavailability with high variability by the approaches of reducing active pharmaceutical ingredient (API) particle size and/or modulating the diffusion layer environment to enhance drug dissolution rate and ultimately in vivo bioavailability.

Formulation techniques used to prevent free acid conversion of the active agent and to enhance its release from the dosage form often disrupts other properties critical to the tablet manufacturing process such as flowability and compaction. Properties such as flowability of formulation material will impact such things as control of the tablet weight, the uniformity of the content of the dosage unit and the ease with which the formulation is able to be fed into a die for compression. Compaction is another critical property necessary to produce tablets with adequate tensile strength and hardness. In addition, it is often desirable to increase the amount of active agent in the dosage form to achieve adequate efficacy in human without increasing the pill size and burden.

There are challenges to develop orally bioavailable dosage forms containing pyrimidinedione compounds due to their extremely low intrinsic aqueous solubility. Although the potassium- or sodium-salt of certain pyrimidinedione compounds possesses a rapid dissolution to form a supersaturated state in aqueous media, the formation of the insoluble free acid form in the physiological GI environment with pH<8 (based on their pKa1>8.3) upon dissolution is inevitable. Therefore, rapid conversion of the salt into the free acid form with essentially extremely slow dissolution usually results in low oral bioavailability. There is therefore a need for improved formulations for poorly water-soluble drugs, and identifying appropriate functional excipients and developing a highly bioavailable drug product of pyrimidinedione compounds continues to be a challenging endeavor.

SUMMARY OF THE INVENTION

The disclosure is directed to pharmaceutical compositions of pyrimidinedione derivative compounds, methods of using such compositions and methods of enhancing the bioavailability of such compounds. In particular, the disclosed pharmaceutical compositions comprise a pyrimidinedione derivative compound, or a salt or hydrate or solvate thereof, or tautomer or combination thereof, and at least one bioavailability enhancing agent.

In embodiments, the compound is N-(6-(3-tert-butyl-5-(2,4-dioxo-3,4-dihydropyrimidin-1(2H)-yl)-2-methoxyphenyl)naphthalen-2-yl)methanesulfonamide (Compound A).

In embodiments, the salt of Compound A is a sodium salt.

In embodiments, the sodium salt of Compound A is a pattern B crystalline monosodium salt.

In embodiments, the pattern B monosodium salt is a monohydrate.

In embodiments, the bioavailability enhancing agent is a polyvinylpyrrolidone.

In embodiments, the bioavailability enhancing agent is present in the pharmaceutical composition in the amount of from about 5% to about 25% by weight of the pharmaceutical composition.

In embodiments, the bioavailability enhancing agent is present in the pharmaceutical composition in the amount of from about 10% to about 25% by weight of the pharmaceutical composition.

In embodiments, the pharmaceutical composition further comprises at least one of the excipients selected from the group consisting of disintegrant, filler, lubricant, and glidant.

In embodiments, the disintegrant is croscarmellose sodium.

In embodiments, the filler is lactose or microcrystalline cellulose.

In embodiments, the lubricant is magnesium stearate.

In embodiments, the glidant is colloidal silicon dioxide.

In embodiments, the pharmaceutical composition is an oral dosage form.

In embodiments, the oral dosage form is a tablet.

In embodiments, the tablet has a tensile strength equal to or greater than 2 Mpa.

The disclosure is also directed to pharmaceutical compositions comprising pyrimidinedione derivative compounds and salts or hydrates or solvates thereof and polyvinylpyrrolidone in an amount of about 5% to about 25% by weight of the pharmaceutical composition.

In embodiments, the compound is N-(6-(3-tert-butyl-5-(2,4-dioxo-3,4-dihydropyrimidin-1(2H)-yl)-2-methoxyphenyl)naphthalen-2-yl)methanesulfonamide (Compound A).

In embodiments, the salt of Compound A is a sodium salt.

The disclosure is further directed to pharmaceutical composition comprising a pattern B monosodium salt of N-(6-(3-tert-butyl-5-(2,4-dioxo-3,4-dihydropyrimidin-1(2H)-yl)-2-methoxyphenyl)naphthalen-2-yl)methanesulfonamide monohydrate, and polyvinylpyrrolidone in an amount of about 10% to about 25% by weight of the pharmaceutical composition.

The disclosure is yet further directed to methods of enhancing bioavailability of a pyrimidinedione derivative compound in a subject comprising preparing a pharmaceutical composition comprising at least one bioavailability enhancing agent and the pyrimidinedione derivative compound, and administering the pharmaceutical composition to a subject.

In an embodiment, the pyrimidinedione derivative compound is N-(6-(3-tert-butyl-5-(2,4-dioxo-3,4-dihydropyrimidin-1(2H)-yl)-2-methoxyphenyl)naphthalen-2-yl)methanesulfonamide (Compound A), or salt or hydrate or solvate thereof.

In embodiments, the bioavailability of the pyrimidinedione derivative compound in the subject is enhanced by at least 30%.

In addition, the disclosure is directed to method of reducing the amount of a pyrimidinedione derivative compound in a pharmaceutical composition necessary to achieve in a subject substantially the same bioavailability of the pyrimidinedione derivative compound in the subject comprising preparing a pharmaceutical composition comprising at least one bioavailability enhancing agent and the pyrimidinedione derivative compound, and administering the pharmaceutical composition to the subject.

In an embodiment, the pyrimidinedione derivative compound is N-(6-(3-tert-butyl-5-(2,4-dioxo-3,4-dihydropyrimidin-1(2H)-yl)-2-methoxyphenyl)naphthalen-2-yl)methanesulfonamide (Compound A), or salt or hydrate or solvate, and administering the pharmaceutical composition to the subject.

In embodiments, the amount of pyrimidinedione derivative compound in the pharmaceutical composition is reduced by at least 30%.

The disclosure is also directed to methods for preparing a pharmaceutical product comprising a pyrimidinedione derivative compound, the method comprising combining the compound with at least one bioavailability enhancing agent in an amount of about 10% to about 25% by weight of the pharmaceutical composition.

The disclosure is further directed to methods of improving tabletability of a pharmaceutical composition comprising a pyrimidinedione derivative compound. The methods comprise combining the compound with at least one bioavailability enhancing agent in an amount of about 10% to about 25% by weight of the pharmaceutical composition.

The disclosure is also directed, in part, to methods of improving bioavailability while maintaining good flowability and compaction of a pharmaceutical composition comprising a pyrimidinedione derivative compound.

In embodiments, the pharmaceutical composition comprises Compound A, or a pharmaceutically acceptable salt thereof; and a pharmaceutically acceptable stabilizing polymer, or combination of pharmaceutically acceptable stabilizing polymers; wherein the pharmaceutical composition comprises the stabilizing polymer, or combination of stabilizing polymers, in an amount of at least about 5% by weight of the pharmaceutical composition.

In embodiments, the pharmaceutical composition comprises Compound A, or a pharmaceutically acceptable salt thereof in an amount of about 200 mg to about 300 mg on a free acid equivalent weight basis; and a pharmaceutically acceptable stabilizing polymer, or combination of pharmaceutically acceptable stabilizing polymers; wherein the pharmaceutical composition comprises the stabilizing polymer, or combination of stabilizing polymers, in an amount of at least about 5% by weight of the pharmaceutical composition.

In embodiments, the pharmaceutical composition comprises Compound A, or a pharmaceutically acceptable salt thereof; and a pharmaceutically acceptable stabilizing polymer, or combination of pharmaceutically acceptable stabilizing polymers; wherein the stabilizing polymer, or combination of stabilizing polymers, inhibit precipitation of Compound A, or a salt thereof.

In embodiments, the pharmaceutical composition comprises Compound A, or a pharmaceutically acceptable salt thereof; and a pharmaceutically acceptable stabilizing polymer, or combination of pharmaceutically acceptable stabilizing polymers; wherein the stabilizing polymer, or combination of stabilizing polymers, inhibit precipitation of Compound A, or a salt thereof and wherein inhibition of precipitation of Compound A, or a salt thereof is determined by the process comprising:

(i) preparing a test solution comprising Compound A, or a salt thereof, and the stabilizing polymer, or combination of stabilizing polymers;

(ii) preparing a control solution, said control solution being substantially identical to the test solution except that said control solution does not contain the stabilizing polymer, or combination of stabilizing polymers;

(iii) maintaining the test mixture and the control solution under the same conditions for a test period; and (iv) determining at the end of the test period the extent to which precipitation of Compound A, or a salt thereof, is inhibited in the test solution relative to the control solution.

In embodiments, the pharmaceutical composition comprises Compound A, or a pharmaceutically acceptable salt thereof; and a pharmaceutically acceptable stabilizing polymer, or combination of pharmaceutically acceptable stabilizing polymers in an amount of at least about 5% by weight of the pharmaceutical composition; wherein the stabilizing polymer, or combination of stabilizing polymers, is selected from the group consisting of copovidone, polyvinylpyrrolidone, hydroxymethylpropylcellulose, SOLUPLUS®, and combinations thereof; wherein the hydroxymethylpropylcellulose has a viscosity less than about 100 centipoise in a 2% solution of at a temperature of about 20° C.

In embodiments, the pharmaceutical composition comprises Compound A, or a pharmaceutically acceptable salt thereof in an amount of about 200 mg to about 300 mg on a free acid equivalent weight basis; and a pharmaceutically acceptable stabilizing polymer, or combination of pharmaceutically acceptable stabilizing polymers in an amount of at least about 5% by weight of the pharmaceutical composition; wherein the stabilizing polymer, or combination of stabilizing polymers, is selected from the group consisting of copovidone, polyvinylpyrrolidone, hydroxymethylpropylcellulose, SOLUPLUS®, and combinations thereof; wherein the hydroxymethylpropylcellulose has a viscosity less than about 100 centipoise in a 2% solution of at a temperature of about 20° C.

In embodiments, the pharmaceutical composition comprises Compound A, or a pharmaceutically acceptable salt thereof; and a pharmaceutically acceptable stabilizing polymer, or combination of pharmaceutically acceptable stabilizing polymers in an amount of at least about 5% by weight of the pharmaceutical composition; wherein the stabilizing polymer, or combination of stabilizing polymers, comprises copovidone.

In embodiments, the pharmaceutical composition comprises Compound A, or a pharmaceutically acceptable salt thereof in an amount of about 200 mg to about 300 mg on a free acid equivalent weight basis; and a pharmaceutically acceptable stabilizing polymer, or combination of pharmaceutically acceptable stabilizing polymers in an amount of at least about 5% by weight of the pharmaceutical composition; wherein the stabilizing polymer, or combination of stabilizing polymers, comprises copovidone.

In embodiments, the pharmaceutical composition is a tablet comprising Compound A, or a pharmaceutically acceptable salt thereof; and a pharmaceutically acceptable stabilizing polymer, or combination of pharmaceutically acceptable stabilizing polymers; wherein the pharmaceutical composition comprises the stabilizing polymer, or combination of stabilizing polymers, in an amount of at least about 5% by weight of the pharmaceutical composition and wherein the tablet when administered as a single dose to a population of human subjects provides an average $AUC_{24}$ value that is at least about 4500 ng·hr/mL for the population of human subjects.

In embodiments, the pharmaceutical composition is a tablet comprising Compound A, or a pharmaceutically acceptable salt thereof; and a pharmaceutically acceptable stabilizing polymer, or combination of pharmaceutically acceptable stabilizing polymers; wherein the pharmaceutical composition comprises the stabilizing polymer, or combination of stabilizing polymers, in an amount of at least about 5% by weight of the pharmaceutical composition and wherein the tablet when administered as a single dose to a population of human subjects provides an average $C_{max}$ value that is less than about 1200 ng/mL for the population of human subjects.

In embodiments, the disclosure is directed to methods for treating hepatitis C in a subject in need of such treatment, wherein the method comprises administering to the subject a pharmaceutical composition of the present disclosure.

In embodiments, the disclosure is directed to methods for treating hepatitis C in a subject in need of such treatment, wherein the method comprises administering to the subject a pharmaceutical composition of the present disclosure with one or more additional therapeutic agents.

BRIEF DESCRIPTION OF THE DRAWINGS

FIG. 13-A Concentration-time profiles for Compound A in buffer without stabilizing polymer (control).
FIG. 13-B Concentration-time profiles for Compound A in 0.001%, 0.01%, and 0.1% Kollidon VA64/buffer.
FIG. 13-C Concentration-time profiles for Compound A in 0.001%, 0.01%, and 0.1% HPMC E5/buffer.
FIG. 13-D Concentration-time profiles for Compound A in 0.001%, 0.01%, and 0.1% HPMC K3/buffer.
FIG. 13-E Concentration-time profiles for Compound A in 0.001%, 0.01%, and 0.1% PVP K30/buffer.
FIG. 13-F Concentration-time profiles for Compound A in 0.001%, 0.01%, and 0.1% Vitamin E TPGS/buffer.

DETAILED DESCRIPTION

Figure 1:
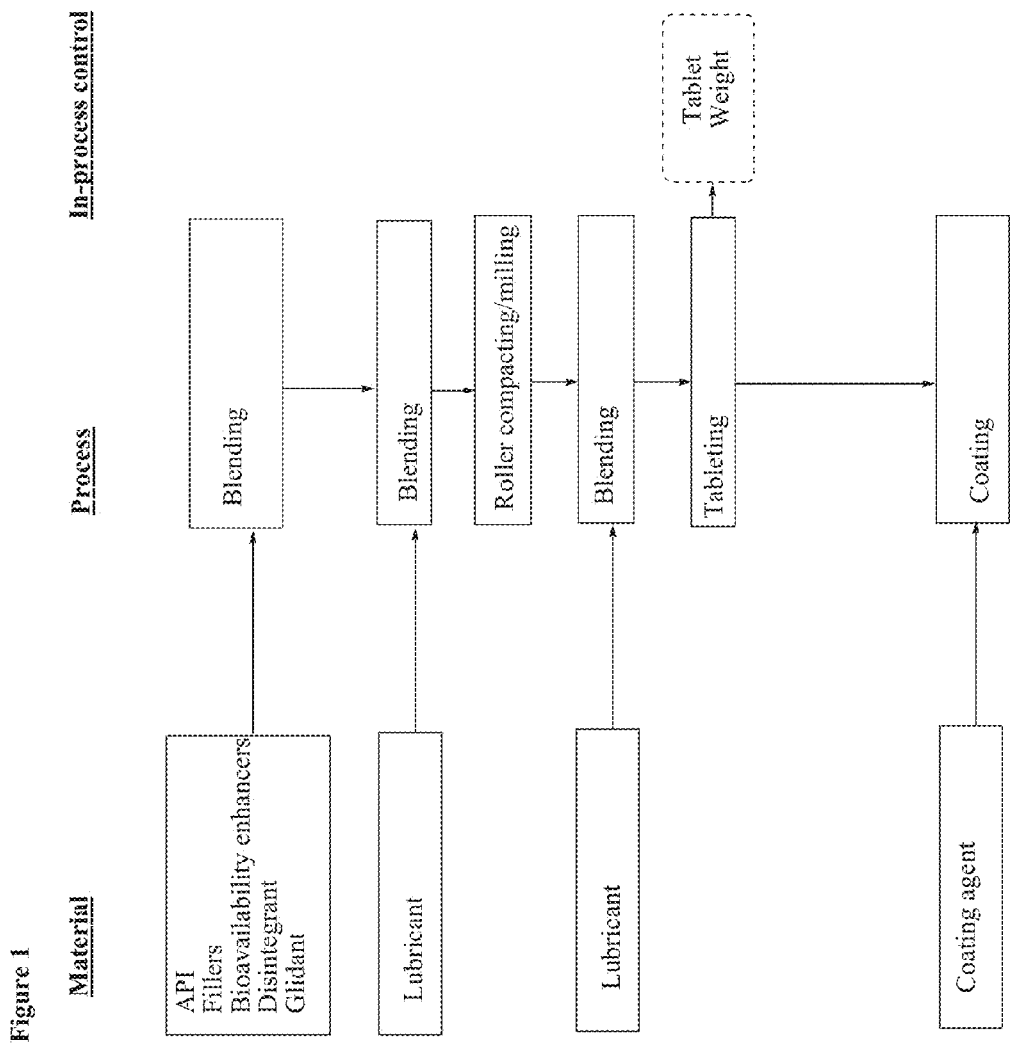
FIG. 1 Roller compaction tablet formulation process flow diagram.

The disclosure is directed to pharmaceutical compositions of pyrimidinedione derivative compounds, methods of using such compositions and methods of enhancing the bioavailability of such compounds. In particular, the disclosed pharmaceutical compositions comprise a pyrimidinedione derivative compound, or a salt or hydrate or solvate thereof, or tautomer or combination thereof, and at least one bioavailability enhancing agent.

The pyrimidinedione derivative compounds may include compounds disclosed in International Publication No. WO 2009/039127 and International Publication No. WO 2009/039134, the entirety of which are incorporated herein by reference, and at least one bioavailability enhancing agent.

The pyrimidinedione derivative compounds disclosed in International Publication No. WO 2009/039127 include compounds represented by the general formula I comprising a moiety having at least one of the nitrogen atoms of the uracil ring attached to a phenyl moiety.

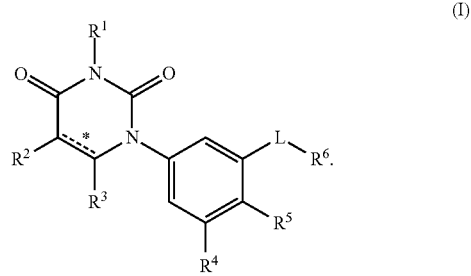

(I)

The pyrimidinedione and phenyl moieties may be further substituted by $R^1$, $R^2$, $R^3$, $R^4$, $R^5$ and $R^6$ as described in WO 2009/039127.

In embodiments, the particle size of the pyrimidinedione derivative compound may be sized using any suitable method to a D50 particle size of from about 10 µm to about 80 µm or from about 30 µm to about 50 µm. In embodiments, the D50 particle size of the pheny uracil derivative active agent is about 20 µm. In embodiments, the D50 particle size of the pheny uracil derivative active agent is about 30 µm. In embodiments, the D50 particle size of the pheny uracil derivative active agent is about 40 µm. In embodiments, the D50 particle size of the pheny uracil derivative active agent is about 50 µm.

The pharmaceutical compositions and formulations of pyrimidinedione derivative compounds include at least one bioavailability enhancing agent. Without being bound to any particular theory, the inclusion of bioavailability enhancing agents in the formulations of pyrimidinedione derivative compounds may sustain the supersaturated state of pyrimidinedione derivative compounds by optimizing the dissolution rate and retarding the precipitation of free acid form. In one embodiment, the bioavailability enhancing agent comprises a pharmaceutically acceptable stabilizing polymer, or combination of pharmaceutically acceptable stabilizing polymers.

As referred to herein, a "bioavailability enhancing agent" is an agent that increases the bioavailability of a pyrimidinedione derivative compound formulation relative to the bioavailability of the same pharmaceutical composition without the bioavailability enhancing agent. In embodiments, the bioavailability enhancing agent enables the bioavailability of a pyrimidinedione derivative compound formulation to increase by at least 10% of the bioavailability of the same pharmaceutical composition without the bioavailability enhancing agent. In embodiments, the bioavailability enhancing agent enables the bioavailability of a pyrimidinedione derivative compound formulation to increase by at least 20%. In embodiments, the bioavailability enhancing agent enables the bioavailability of a pyrimidinedione derivative compound formulation to increase by at least 30%. Bioavailability may be measured by any suitable parameter including pharmacokinetic parameters, such as AUC and $C_{max}$, and pharmacodynamic parameters. Enhanced bioavailability of a pharmaceutical composition may also be measured by how much less drug load is required to achieve the same bioavailability in a pharmaceutical composition with a higher drug load and without the bioavailability enhancing agent.

Bioavailability enhancing agents may include water soluble low molecular weight polymers. Bioavailability enhancing agents may include for example, hydroxypropylcellulose (HPC) such as Methocel E5; polyvinyl pyrolidone (PVP) such as PVP K30; copovidone (vinylpyrrolidone-vinyl acetate copolymers) such as Kollidon® VA64 fine, Kollidon® CL-M; polyvinylpyrrolidonehydroxypropyl cellulose; hydroxypropylmethylcellulose such as HPMC-E5, HPMC-AS (acetate succinate), HPMC-P55, starch, HPMC-AS, Lutrol F127, polyethylene oxide, acrylic acid polymers such as Eudragit, and any other suitable bioavailability enhancing agent and combinations thereof. In one embodiment, the bioavailability enhancing agent is a stabilizing polymer, or combination of stabilizing polymers (e.g., copovidone, polyvinylpyrrolidone, hydroxymethylpropylcellulose having a viscosity less than about 100 centipoise at its 2% solution, SOLUPLUS®, and combinations thereof).

In embodiments, the bioavailability enhancing agent is present in the pharmaceutical composition in the amount of from about 3 percent to about 50 percent by weight of the weight of the pharmaceutical composition (w/w) or from about 5 percent to about 40 percent (w/w) or from about 10 percent to about 30 percent (w/w) or from about 15 percent to about 25 percent (w/w). In embodiments, the pharmaceutical composition includes at least one bioavailability enhancing agent in the amount of about 5 percent (w/w). In embodiments, the pharmaceutical composition includes at least one bioavailability enhancing agent in the amount of about 15 percent (w/w). In embodiments, the pharmaceutical composition includes at least one bioavailability enhancing agent in the amount of about 20 percent w/w. In embodiments, the pharmaceutical composition includes at least one bioavailability enhancing agent in the amount of about 25 percent w/w.

The pharmaceutical compositions of the pyrimidinedione derivative may comprise other excipients such as excipients that function as fillers, disintegrants, glidants and lubricants.

In embodiments, the disclosed pharmaceutical compositions comprise at least one excipient that functions as a filler. Fillers may include calcium hydrogenphosphate, microcrystalline cellulose (Avicel®), natural or pre-gelatinized potato or corn starch, or any other suitable bulking agent. Examples of suitable fillers include microcrystalline cellulose, such as Avicel PH 101, Avicel PH102, Avicel PH 200, Avicel PH 105, Avicel DG, Ceolus KG 802, Ceolus KG 1000, SMCC50 and Vivapur 200; lactose monohydrate, such as Lactose FastFlo; microcrystalline cellulose co-processed with other excipients, such as microcrystalline cellulose co-processed with lactose monohydrate (MicroceLac 100) and microcrystalline cellulose co-processed with colloidal silicon dioxide (SMCC50, Prosolv 50 and Prosolv HD 90); mixtures of isomaltulose derivatives such as galenIQ; and other suitable fillers and combinations thereof.

In embodiments, the one or more fillers are present in the pharmaceutical composition in the amount of from about 5 percent to about 60 percent by weight of the weight of the pharmaceutical composition (w/w), or from about 10 percent to about 50 percent w/w, or from about 20 percent to about 40 percent w/w.

In embodiments, filler is included in an intragranular portion of the pharmaceutical composition. In embodiments, no filler is included in the intragranular portion of the pharmaceutical composition. In embodiments, about 5 percent to about 17 percent filler is included in the intragranular portion of the pharmaceutical composition.

In embodiments, filler is included in an extragranular portion of the pharmaceutical composition. In embodiments, about 10 percent to about 45 percent filler is included in the extragranular portion of the pharmaceutical composition. In embodiments, about 12 percent filler is included in the extragranular portion of the pharmaceutical composition. In embodiments, about 16 percent filler is included in the extragranular portion of the pharmaceutical composition. In embodiments, about 22 percent filler is included in the extragranular portion of the pharmaceutical composition. In embodiments, about 36 percent filler is included in the extragranular portion of the pharmaceutical composition. In embodiments, about 42 percent filler is included in the extragranular portion of the pharmaceutical composition.

In embodiments, filler is included in both an intragranular portion and an extragranular portion of the pharmaceutical composition. In embodiments, about 5 percent filler is included in the intragranular portion of the pharmaceutical composition and about 10 percent filler is included in the extragranular portion of the pharmaceutical composition. In embodiments, about 12 percent filler is included in the intragranular portion of the pharmaceutical composition and about 25 percent filler is included in the extragranular portion of the pharmaceutical composition. In embodiments, about 15 percent filler is included in the intragranular portion of the pharmaceutical composition and about 30 percent filler is included in the extragranular portion of the pharmaceutical composition. In embodiments, about 17 percent filler is included in the intragranular portion of the pharmaceutical composition and about 35 percent filler is included in the extragranular portion of the pharmaceutical composition.

In embodiments, the pharmaceutical composition includes a first filler in the amount of about 30 percent w/w and a second filler in the amount of about 7 percent w/w. In embodiments, the pharmaceutical composition includes a first filler in the amount of about 25 percent w/w and a second filler in the amount of about 7 percent w/w. In embodiments, the pharmaceutical composition includes a first filler in the amount of about 20 percent w/w and a second filler in the amount of about 7 percent w/w. In embodiments, the first filler is Avicel PH 105 and the second filler is lactose monohydrate. In embodiments, the pharmaceutical composition includes a first filler in the amount of about 15 percent w/w, a second filler in the amount of about 15 percent w/w, and a third filler in the amount of about 7 percent w/w. In embodiments, the first filler is Avicel PH 101, the second filler is Avicel PH 102, and the third filler is lactose monohydrate.

Disintegrants may be included in the disclosed formulations to promote separation of the granules within the compact from one another and to maintain separation of the liberated granules from one another. Disintegrants may include any suitable disintegrant such as, for example, crosslinked polymers such as cross-linked polyvinyl pyrrolidone and cross-linked sodium carboxymethylcellulose or sodium croscarmellose. In embodiments, the disintegrant is croscarmellose sodium.

The pharmaceutical composition may include any suitable amount of one or more disintegrants including, for example, from about 2 percent to about 10 percent w/w or from about 3 percent to about 7 percent w/w/of the pharmaceutical composition. In embodiments, the pharmaceutical composition includes about 5 percent croscarmellose sodium. The pharmaceutical composition may include any suitable amount of disintegrant including, for example, from about 2 percent to about 20 percent w/w or from about 5 percent to about 15 percent of the pharmaceutical product.

In embodiments, disintegrant is included in an intragranular portion of the pharmaceutical composition. In embodiments, about 2 percent to about 5 percent disintegrant is included in the intragranular portion of the pharmaceutical composition. In embodiments, about 3 percent disintegrant is included in the intragranular portion of the pharmaceutical composition.

In embodiments, disintegrant is included in an extragranular portion of the pharmaceutical composition. In embodiments, about 2 percent to about 15 percent disintegrant is included in the extragranular portion of the pharmaceutical composition. In embodiments, about 5 percent disintegrant is included in the extragranular portion of the pharmaceutical composition. In embodiments, about 10 percent filler is included in the extragranular portion of the pharmaceutical composition.

Glidants may include, for example, colloidal silicon dioxide, including highly dispersed silica (Aerosil®) or any other suitable glidant such as animal or vegetable fats or waxes in any suitable amounts including, for example, from about 0.1 percent to about 2 percent w/w of the pharmaceutical product, or from about 0.3 percent to 1.2 percent glidant, or from about 0.5 percent to 1 percent glidant. In embodiments, the pharmaceutical composition includes about 0.6 percent w/w colloidal silicon dioxide.

Lubricants may be used in compacting granules in the pharmaceutical composition. Lubricants may include, for example, polyethylene glycol (e.g., having a molecular weight of from about 1000 to about 6000), magnesium and calcium stearates, sodium stearyl fumarate, talc, or any other suitable lubricant in any suitable amounts including, for example, from about 0.1 percent to about 10 percent w/w, or from about 0.3 percent to about 8 percent w/w of the pharmaceutical composition, or from about 0.5 percent to about 2 percent w/w. In embodiments, the lubricant is magnesium stearate. In embodiments, the pharmaceutical composition includes about 1.65 percent w/w magnesium stearate.

In embodiments, lubricant is included in an intragranular portion of the pharmaceutical composition. In embodiments, lubricant is included in an extragranular portion of the pharmaceutical composition. In embodiments, extragranular excipients include about 0.5 percent lubricant.

For example, as set forth in Table 1, the disclosed pharmaceutical compositions may include one or more fillers, disintegrants, glidants and lubricants in combination with the active agent and bioavailability enhancement agent.

TABLE 1

| Ingredient | Formulation 1 | Formulation 2 | Formulation 3 | Formulation 4 |
|---|---|---|---|---|
| | % w/w | | | |
| Active Agent | 40.00 | 40.00 | 40.00 | 40.00 |
| Bioavailability Enhancing Agent | 15.00 | 20.00 | 25.00 | 5.00 |
| Filler | 37.75 | 32.00 | 28.00 | 47.00 |
| Disintegrant | 5.00 | 5.00 | 5.00 | 5.00 |
| Glidant | 0.60 | 1.00 | 0 | 1.00 |
| Lubricant | 1.65 | 2.00 | 2.00 | 2.00 |
| Total | 100.00 | 100.00 | 100.00 | 100.00 |

The pharmaceutical composition may also include formulations of pyrimidinedione derivatives that comprise at least one excipient that functions as a surfactant, at least one excipient that functions as an alkalizing agent, at least one excipient that functions as a flow regulator or combinations thereof.

Surfactant may be included in the formulation to increase the concentration of the drug in the diffusion layer or increase wettability of the drug/formulation. In embodiments, the surfactant may include, for example, vitamin E d-alpha tocopheryl polyethyleneglycol succinate (Vit E TPGS), sodium dodecyl sulfate (SDS), polysorbate, poloxamer and other suitable surfactants. The pharmaceutical composition may include any suitable amount of surfactant including, for example, about 0 percent to about 10 percent w/w or from about 1 percent to about 6 percent w/w of the pharmaceutical product. In embodiments, the amount of surfactant in the pharmaceutical product is about 5 percent w/w of the pharmaceutical product. In embodiments, the surfactant is included in an intragranular portion of the pharmaceutical composition.

In embodiments, the pharmaceutical composition of the pyrimidinedione derivative comprises at least one excipient that functions as an alkalizing agent or base buffering agent. Alkalizing agents or pH modifiers may be used to maintain higher pH in the diffusion layer to contribute to inhibiting free acid conversion. Agents with a pKa value greater than the pKa of the drug can be used as alkalizing agents. Alkalizing agents may include, for example, sodium carbonate, sodium bicarbonate, Meglumine or any other suitable alkalizing agent. The pharmaceutical composition may include any suitable amount alkalizing agent including, for example, from about 0 percent to about 8 percent w/w or from about 0 percent to about 5 percent of the pharmaceutical product. In embodiments, the amount of alkalizing agent in the pharmaceutical product is about 5 percent w/w of the pharmaceutical product. In embodiments, the alkalizing agent is included in an intragranular portion of the pharmaceutical composition.

Suitable flow regulators are selected from highly dispersed silica (Aerosil®), and animal or vegetable fats or waxes.

Alternatively or in addition, various other additives may be used such as, for example, dyes, such as azo dyes, organic or inorganic pigments, such as aluminum oxide or titanium dioxide, or dyes of natural origin; stabilizers such as antioxidants, light stabilizers, radical scavengers, or stabilizers against microbial attack.

The disclosed pharmaceutical compositions may be prepared by any suitable method. Methods such as direct compression, roller compaction or dry granulation and wet granulation may be used to blend the pyrimidinedione derivative with the bioavailability enhancing agent and any other excipients of the pharmaceutical composition.

In embodiments, the disclosed pharmaceutical compositions are prepared using a roller compaction process. The roller compaction process may include any suitable steps. As illustrated in FIG. 1, roller compaction may include steps such as blending the active agent with one or more intragranular excipients sized for blending; feeding the blend into a roller compactor to densify loose powder into ribbons; milling the resultant ribbons into granules; optionally blending the granules with extragranular excipients such as lubricants and compressing the granules into tablets or encapsulating the granules into capsules.

In embodiments, the disclosed pharmaceutical compositions are prepared using a wet granulation process and by compressing the final blend into tablets or encapsulating the granules into capsules.

The disclosed tablets may be coated with any suitable coating such as a film coat. A film coat may be used to, for example, contribute to the ease with which the tablet can be swallowed. A film coat may also be employed to improve taste and provide an elegant appearance. If desired, the film coat may be an enteric coat. The film coat may comprise a polymeric film-forming material such as hydroxypropyl methylcellulose, hydroxypropyl cellulose, acrylate or methacrylate copolymers, and polyvinyl alcohol-polyethylene glycol graft copolymers such as Opadry and Kollicoat IR. In addition to a film-forming polymer, the film coat may further comprise a plasticizer, e.g. polyethylene glycol, a surfactant, e.g. a Tween® type, and optionally a pigment, e.g. titanium dioxide or iron oxides. The film-coating may also comprise talc as an anti-adhesive. The film coat may account for less than about 5% by weight of the dosage form. In order to facilitate the intake of such a dosage form by a mammal, the dosage form may be shaped into an appropriate shape such as a round or elongated shape.

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other excipients and modes of administration known in the pharmaceutical art also may be used.

The disclosed pharmaceutical compositions may be used for inhibiting replication of an RNA virus. The method comprises exposing the virus to one or more of the disclosed pharmaceutical compositions. In embodiments, the RNA virus whose replication is being inhibited is a single-stranded, positive sense RNA virus. In some such embodiments, the RNA virus whose replication is being inhibited is a virus from the Flaviviridae family. In some such embodiments, the RNA virus whose replication is being inhibited is hepatitis C virus (HCV).

The disclosed pharmaceutical compositions may be used for inhibiting HCV RNA polymerase. The method comprises exposing the polymerase to one or more of the disclosed pharmaceutical compositions.

The term "inhibiting" means reducing the level of RNA virus replication/HCV polymerase activity either in vitro or in vivo. For example, if a disclosed pharmaceutical composition reduces the level of RNA virus replication by at least about 10% compared to the level of RNA virus replication before the virus was exposed to the composition, then the disclosed pharmaceutical composition inhibits RNA virus replication. In embodiments, the disclosed pharmaceutical compositions can inhibit RNA virus replication by at least about 20%, at least about 30%, at least about 40%, at least about 50%, at least about 60%, at least about 70%, at least about 80%, at least about 90%, or at least about 95%.

The disclosed pharmaceutical compositions may be used for treating a disease that can be treated by inhibiting HCV RNA polymerase. Thus, the disclosed pharmaceutical compositions may also be used for treating hepatitis C in an animal in need of such treatment. These methods comprise administering to the animal one or more of the disclosed pharmaceutical compositions, and, optionally, one or more additional therapeutic agents. "Treating" means ameliorating, suppressing, eradicating, preventing, reducing the risk of, and/or delaying the onset of the disease being treated. Applicants specifically intend that the term "treating" encompass administration of the disclosed pharmaceutical compositions to an HCV-negative patient that is a candidate for an organ transplant. The methods of treatment are particularly suitable for use with humans, but may be used with other animals, particularly mammals.

In embodiments, the methods comprise combination therapy, wherein the disclosed pharmaceutical compositions are co-administered with a second (or even a third, fourth, etc.) composition, such as, for example, a composition containing another therapeutic agent used to treat hepatitis C (e.g., interferon or interferon/ribavirin combination, or an HCV inhibitor such as, for example, an HCV polymerase inhibitor or an HCV protease inhibitor or an NS5a inhibitor). The disclosed pharmaceutical compositions can also be co-administered with therapeutic agents other than therapeutic agents used to treat hepatitis C (e.g., anti-HIV agents). In these co-administration embodiments, the disclosed pharmaceutical compositions and the second, etc. composition(s) may be administered in a substantially simultaneous manner (e.g., or within about 5 minutes of each other), in a sequential manner, or both. It is contemplated that such combination therapies may include administering one composition multiple times between the administrations of the other. The time period between the administration of each composition may range from a few seconds (or less) to several hours or days, and will depend on, for example, the properties of each composition and active ingredient (e.g., potency, solubility, bioavailability, half-life, and kinetic profile), as well as the condition of the patient. The disclosed pharmaceutical compositions and the second, etc. composition may also be administered in a single formulation.

Additional Embodiments

Compound A

N-(6-(3-tert-butyl-5-(2,4-dioxo-3,4-dihydropyrimidin-1 (2H)-yl)-2-methoxyphenyl)naphthalen-2-yl)methanesulfonamide (Compound A) is a free acid that exhibits good permeability but poor solubility in the gastrointestinal tract. Administering a salt of Compound A (such as the sodium salt) rather than the free acid form of Compound A, however, does not improve Compound A solubility and uptake in the gastrointestinal tract to the extent expected. As illustrated by the studies reported in the Examples, the incorporation of a stabilizing polymer, or combination of stabilizing polymers, in pharmaceutical compositions comprising Compound A, or a salt thereof, results in improved in vivo performance relative to corresponding pharmaceutical compositions that do not contain the stabilizing polymer, or combination of stabilizing polymers.

It is hypothesized that in pharmaceutical compositions comprising a salt of Compound A but lacking a sufficient amount of the stabilizing polymer, or combination of stabilizing polymers, the salt is rapidly converted to the relatively insoluble free acid when the salt comes into contact with the acidic environment of the stomach. The free acid then precipitates on the surface of the solid pharmaceutical composition without being released into the surrounding medium and/or precipitates out of the surrounding medium. This precipitation of the free acid results in a smaller amount of the administered dose of Compound A dissolving in the medium and being available for uptake and lowers the overall bioavailability of Compound A. It is further hypothesized that the incorporation of the stabilizing polymer, or combination of stabilizing polymers, in the pharmaceutical composition creates a microenvironment in the gastrointestinal tract in which the salt of Compound A dissolves to provide the free acid and the stabilizing polymer, or combination of stabilizing polymers, then functions to maintain the free acid in a supersaturated state in solution rather than precipitating out of solution. Because the amount of dissolved free acid increases and free acid precipitation is reduced, a larger amount of the administered dose is absorbed and the bioavailability of Compound A is increased.

As a result, the drug loading in a unit dose formulation comprising a salt of Compound A and a stabilizing polymer, or combination of stabilizing polymers, can be reduced (e.g., by about 20% to 30%) without a reduction in Compound A bioavailability relative to a similar unit dose formulation having a higher drug loading but otherwise lacking a sufficient amount of the stabilizing polymer, or combination of stabilizing polymers. By facilitating a reduction in the required drug loading of the unit dosage form, the stabilizing polymer, or combination of stabilizing polymers, effectively facilitates a corresponding reduction in the size of the unit dosage form where desirable. The results reported in the Examples are consistent with the hypothesized mechanism of action.

In one embodiment, the present disclosure relates to pharmaceutical compositions comprising Compound A, or a pharmaceutically acceptable salt thereof, and a pharmaceutically acceptable stabilizing polymer, or combination of pharmaceutically acceptable stabilizing polymers. In one aspect, the pharmaceutical composition comprises a salt of Compound A and a stabilizing polymer, or combination of stabilizing polymers. In another aspect, the salt of Compound A is an alkali metal salt. In another aspect, the salt of Compound A is a sodium salt. In another aspect, the sodium salt of Compound A is a pattern B crystalline monosodium salt. In another aspect, the pattern B monosodium salt is a pattern B monosodium salt monohydrate.

In another embodiment, the present disclosure relates to pharmaceutical compositions comprising from about 200 mg to about 300 mg of Compound A, or a pharmaceutically acceptable salt thereof, on a free acid equivalent weight basis, and a pharmaceutically acceptable stabilizing polymer, or combination of pharmaceutically acceptable stabilizing polymers. In one aspect, the amount of Compound A, or salt thereof, is about 225 mg to about 275 mg on a free acid equivalent weight basis. In another aspect, the amount of Compound A, or salt thereof, is about 240 mg to about 260 mg on a free acid equivalent weight basis. In another aspect, the amount of Compound A, or salt thereof, is about 245 mg to about 255 mg on a free acid equivalent weight basis. In another aspect, the amount of Compound A, or salt thereof, is about 250 mg on a free acid equivalent weight basis.

In another embodiment, the present disclosure relates to pharmaceutical compositions comprising an amount of Compound A, or a pharmaceutically acceptable salt thereof, that is at least about 20% by weight of the pharmaceutical composition on a free acid equivalent weight basis, and a pharmaceutically acceptable stabilizing polymer, or combination of pharmaceutically acceptable stabilizing polymers. In one aspect, the amount of Compound A, or salt thereof, is at least about 30% by weight of the pharmaceutical composition on a free acid equivalent weight basis. In another aspect, the amount of Compound A, or salt thereof, is about 30% to about 60% percent by weight of the pharmaceutical composition on a free acid equivalent weight basis. In another aspect, the amount of Compound A, or salt thereof, is about 30% to about 50% percent by weight of the pharmaceutical composition on a free acid equivalent weight basis. In another aspect, the amount of Compound A, or salt thereof, is about 35% to about 45% percent by weight of the pharmaceutical composition on a free acid equivalent weight basis. In another aspect, the amount of Compound A, or salt thereof, is about 40% by weight of the pharmaceutical composition on a free acid equivalent weight basis.

In another embodiment, the present disclosure relates to pharmaceutical compositions comprising Compound A, or a pharmaceutically acceptable salt thereof, and a pharmaceutically acceptable stabilizing polymer, or combination of pharmaceutically acceptable stabilizing polymers, wherein the amount of the stabilizing polymer, or combination of stabilizing polymers, is about 5% by weight of the pharmaceutical composition. In one aspect, the amount of the stabilizing polymer, or combination of stabilizing polymers, is at least about 10% by weight of the pharmaceutical composition. In another aspect, the amount of the stabilizing polymer, or combination of stabilizing polymers, is at least about 15% by weight of the pharmaceutical composition. In another aspect, the amount of the stabilizing polymer, or combination of stabilizing polymers, is about 15% by weight of the pharmaceutical composition. In another aspect, the amount of the stabilizing polymer, or combination of stabilizing polymers, is about 5% to about 50% by weight of the pharmaceutical composition. In another aspect, the amount of the stabilizing polymer, or combination of stabilizing polymers, is about 5% to about 40% by weight of the pharmaceutical composition. In another aspect, the amount of the stabilizing polymer, or combination of stabilizing polymers, is about 5% to about 25% by weight of the pharmaceutical composition. In another aspect, the amount of the stabilizing polymer, or combination of stabilizing polymers, is about 10% to about 50% by weight of the pharmaceutical composition. In another aspect, the amount of the stabilizing polymer, or combination of stabilizing polymers, is about 10% to about 40% by weight of the pharmaceutical composition. In another aspect, the amount of the stabilizing polymer, or combination of stabilizing polymers, is about 10% to about 25% by weight of the pharmaceutical composition. In another aspect, the amount of the stabilizing polymer, or combination of stabilizing polymers, is about 15% by weight of the pharmaceutical composition.

In another embodiment, the present disclosure relates to pharmaceutical compositions comprising Compound A, or a pharmaceutically acceptable salt thereof, and a pharmaceutically acceptable salt stabilizing polymer, or combination of pharmaceutically acceptable salt stabilizing polymers, wherein the weight ratio of the stabilizing polymer, or combination of stabilizing polymers, to Compound A, or the salt thereof, on a free acid equivalent weight basis is from about 4:1 to about 1:8. In one aspect, the weight ratio of the stabilizing polymer, or combination of stabilizing polymers, to Compound A, or the salt thereof, on a free acid equivalent weight basis is from about 2:1 to about 1:4. In another aspect, the weight ratio of the stabilizing polymer, or combination of stabilizing polymers, to Compound A, or the salt thereof, on a free acid equivalent weight basis is from about 1:1 to about 1:3.5. In another aspect, the weight ratio of the stabilizing polymer, or combination of stabilizing polymers, to Compound A, or the salt thereof, on a free acid equivalent weight basis is from about 1:1.5 to about 1:3.5. In another aspect, the weight ratio of the stabilizing polymer, or combination of stabilizing polymers, to Compound A, or the salt thereof, on a free acid equivalent weight basis is from about 1:2 to about 1:3.

In another embodiment, the present disclosure relates to pharmaceutical compositions comprising:
Compound A, or a pharmaceutically acceptable salt thereof, in an amount of about 200 mg to about 300 mg on a free acid equivalent weight basis; and
a pharmaceutically acceptable stabilizing polymer, or combination of pharmaceutically acceptable stabilizing polymers, in an amount of at least about 5% by weight of the pharmaceutical composition.

In another embodiment, the present disclosure relates to pharmaceutical compositions comprising Compound A, or a pharmaceutically acceptable salt thereof, and a pharmaceutically acceptable stabilizing polymer, or combination of pharmaceutically acceptable stabilizing polymers, wherein the stabilizing polymer, or combination of stabilizing polymers, inhibits precipitation of Compound A, or a salt thereof. In one aspect, the stabilizing polymer, or combination of stabilizing polymers, inhibits precipitation of Compound A, or a salt thereof, by at least 10% relative to a substantially identical pharmaceutical composition that does not contain the stabilizing polymer, or combination of stabilizing polymers. In another aspect, the stabilizing polymer, or combination of stabilizing polymers, inhibits precipitation of Compound A, or a salt thereof, by at least 20%. In another aspect, the stabilizing polymer, or combination of stabilizing polymers, inhibits precipitation of Compound A, or a salt thereof, by at least 30%. In another aspect, the stabilizing polymer, or combination of stabilizing polymers, inhibits precipitation of Compound A, or a salt thereof, by at least 40%. In another aspect, the stabilizing polymer, or combination of stabilizing polymers, inhibits precipitation of Compound A, or a salt thereof, by at least 50%. In another aspect, the stabilizing polymer, or combination of stabilizing polymers, inhibits precipitation of Compound A, or a salt thereof, by at least 60%. In another aspect, the stabilizing polymer, or combination of stabilizing polymers, inhibits precipitation of Compound A, or a salt thereof, by at least 70%. In another aspect, the stabilizing polymer, or combination of stabilizing polymers, inhibits precipitation of Compound A, or a salt thereof, by at least 80%.

In another embodiment, the present disclosure relates to pharmaceutical compositions comprising Compound A, or a pharmaceutically acceptable salt thereof, and a pharmaceutically acceptable stabilizing polymer, or combination of pharmaceutically acceptable stabilizing polymers, wherein the stabilizing polymer, or combination of stabilizing polymers, inhibits precipitation of Compound A, or a salt thereof, and wherein inhibition of precipitation of Compound A, or a salt thereof is determined by the process comprising:
  (i) preparing a test solution comprising Compound A, or a salt thereof, and the stabilizing polymer, or combination of stabilizing polymers;
  (ii) preparing a control solution, said control solution being substantially identical to the test solution except that said control solution does not contain the stabilizing polymer, or combination of stabilizing polymers;
  (iii) maintaining the test mixture and the control solution under the same conditions for a test period; and (iv) determining at the end of the test period the extent to which precipitation of Compound A, or a salt thereof, is inhibited in the test solution relative to the control solution.

In one aspect, the stabilizing polymer, or combination of stabilizing polymers, inhibits precipitation of Compound A, or a salt thereof, by at least 10% relative to a substantially identical pharmaceutical composition that does not contain the stabilizing polymer, or combination of stabilizing polymers. In another aspect, the stabilizing polymer, or combination of stabilizing polymers, inhibits precipitation of Compound A, or a salt thereof, by at least 20%. In another aspect, the stabilizing polymer, or combination of stabilizing polymers, inhibits precipitation of Compound A, or a salt thereof, by at least 30%. In another aspect, the stabilizing polymer, or combination of stabilizing polymers, inhibits precipitation of Compound A, or a salt thereof, by at least 40%. In another aspect, the stabilizing polymer, or combination of stabilizing polymers, inhibits precipitation of Compound A, or a salt thereof, by at least 50%. In another aspect, the stabilizing polymer, or combination of stabilizing polymers, inhibits precipitation of Compound A, or a salt thereof, by at least 60%. In another aspect, the stabilizing polymer, or combination of stabilizing polymers, inhibits precipitation of Compound A, or a salt thereof, by at least 70%. In another aspect, the stabilizing polymer, or combination of stabilizing polymers, inhibits precipitation of Compound A, or a salt thereof, by at least 80%.

In another embodiment, the present disclosure relates to pharmaceutical compositions comprising Compound A, or a pharmaceutically acceptable salt thereof, and a pharmaceutically acceptable stabilizing polymer, or combination of pharmaceutically acceptable stabilizing polymers, wherein the stabilizing polymer, or combination of stabilizing polymers, inhibits precipitation of Compound A, or a salt thereof, and wherein inhibition of precipitation of Compound A, or a salt thereof is determined by the process comprising:
 (a) preparing a test solution, wherein the test solution is prepared by adding (i) about 0.05 mL of a solution comprising Compound A, or a salt thereof, in dimethyl sulfoxide at a concentration of about 16 mg/mL on a free acid equivalent weight basis, to (ii) about 10 mL of a 0.1% solution (weight polymer/volume buffer) of the stabilizing polymer, or combination of stabilizing polymers, in a pH 6.8 sodium phosphate buffer (50 mM phosphate with ionic strength adjusted to 0.155 M with sodium chloride) to provide the test solution;
 (b) preparing a control solution, wherein the control solution is prepared by adding (i) about 0.05 mL of a solution comprising Compound A, or a salt thereof, in dimethyl sulfoxide at a concentration of about 16 mg/mL on a free acid equivalent weight basis, to (ii) about 10 mL of a pH 6.8 sodium phosphate buffer (50 mM phosphate with ionic strength adjusted to 0.155 M with sodium chloride) to provide the control solution;
 (c) maintaining the test solution and the control solution under stirring and at a temperature of about 25° C.±2° C. for a test period of about 30 minutes; and
 (d) determining at the end of the test period the extent to which precipitation of Compound A, or a salt thereof, has been inhibited in the test solution relative to the control solution.

In one aspect, the stabilizing polymer, or combination of stabilizing polymers, inhibits precipitation of Compound A, or a salt thereof, in the test solution relative to the control solution by at least 10%.

In another aspect, the stabilizing polymer, or combination of stabilizing polymers, inhibits precipitation of Compound A, or a salt thereof, by at least 20%. In another aspect, the stabilizing polymer, or combination of stabilizing polymers, inhibits precipitation of Compound A, or a salt thereof, by at least 30%. In another aspect, the stabilizing polymer, or combination of stabilizing polymers, inhibits precipitation of Compound A, or a salt thereof, by at least 40%. In another aspect, the stabilizing polymer, or combination of stabilizing polymers, inhibits precipitation of Compound A, or a salt thereof, by at least 50%. In another aspect, the stabilizing polymer, or combination of stabilizing polymers, inhibits precipitation of Compound A, or a salt thereof, by at least 60%. In another aspect, the stabilizing polymer, or combination of stabilizing polymers, inhibits precipitation of Compound A, or a salt thereof, by at least 70%. In another aspect, the stabilizing polymer, or combination of stabilizing polymers, inhibits precipitation of Compound A, or a salt thereof, by at least 80%.

Suitable methods for determining whether precipitation of Compound A, or a salt thereof, has been inhibited in the test solution relative to the control solution include UV/Vis spectrophotometry using an in situ UV/Vis probe; HPLC assay of the supernant solution after removing particles; and other conventional methods known to those of skill in the art.

In another embodiment, the present disclosure relates to pharmaceutical compositions comprising Compound A, or a pharmaceutically acceptable salt thereof, and a pharmaceutically acceptable stabilizing polymer, or combination of pharmaceutically acceptable stabilizing polymers, wherein the stabilizing polymer, or combination of stabilizing polymers, is selected from the group consisting of copovidone, polyvinylpyrrolidone, hydroxymethylpropylcellulose, SOLUPLUS®, and combinations thereof; wherein the hydroxymethylpropylcellulose has a viscosity less than about 100 centipoise in a 2% solution (i.e., a 2% aqueous solution) at a temperature of about 20° C. In one aspect, the stabilizing polymer, or combination of stabilizing polymers, is selected from the group consisting of copovidone, polyvinylpyrrolidone, hydroxymethylpropylcellulose, and combinations thereof; wherein the hydroxymethylpropylcellulose has a viscosity less than about 100 centipoise in a 2% solution at a temperature of about 20° C. In another aspect, the stabilizing polymer, or combination of stabilizing polymers, comprises copovidone. In another aspect, the stabilizing polymer, or combination of stabilizing polymers, comprises polyvinylpyrrolidone. In another aspect, the stabilizing polymer, or combination of stabilizing polymers, comprises hydroxymethylpropylcellulose having a viscosity less than about 100 centipoise in a 2% solution at a temperature of about 20° C. In another aspect, the stabilizing polymer, or combination of stabilizing polymers, comprises SOLUPLUS®. In another aspect, the pharmaceutical composition comprises two or more stabilizing polymers selected from the group consisting of copovidone, polyvinylpyrrolidone, hydroxymethylpropylcellulose, and SOLUPLUS®; wherein the hydroxymethylpropylcellulose has a viscosity less than about 100 centipoise in a 2% solution at a temperature of about 20° C.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers. In one aspect, the pharmaceutical composition is an immediate release oral dosage form.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein the oral dosage form has a weight less than about 1500 mg. In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to pharmaceutical compositions that are tablets comprising Compound A, or a pharmaceutically acceptable salt thereof, and a pharmaceutically acceptable stabilizing polymer, or combination of pharmaceutically acceptable stabilizing polymers. In one aspect, the tablet has a weight from about 500 mg to about 1500 mg. In another aspect, the tablet has a weight from about 500 mg to about 1300 mg. In another aspect, the tablet has a weight from about 500 mg to about 1100 mg. In another aspect, the tablet has a weight from about 500 mg to about 900 mg. In another aspect, the tablet has a weight from about 500 mg to about 750 mg. In another aspect, the tablet has a weight from about 500 mg to about 750 mg. In another aspect, the tablet has a weight from about 675 mg to about 725 mg. In another aspect, the tablet has a weight of about 700 mg. In another aspect, the tablet is coated with a polymer coating. In another aspect, tablet is coated with an enteric coating.

In another embodiment, the present disclosure relates to pharmaceutical compositions that are oral dosage forms comprising about 250 mg of Compound A, or a pharmaceutically acceptable salt thereof, on a free acid equivalent basis, and a pharmaceutically acceptable stabilizing polymer, or combination of pharmaceutically acceptable stabilizing polymers, and wherein the oral dosage form when administered as a single dose to a population of human subjects provides an average $AUC_{24}$ value that is at least about 4500 ng·hr/mL for the population of human subjects. In one aspect, the oral dosage form when administered as a single dose to a population of human subjects provides an average $AUC_{24}$ value from about 4500 ng·hr/mL to about 9000 ng·hr/mL for the population of human subjects.

In another embodiment, the present disclosure relates to pharmaceutical compositions that are oral dosage forms comprising about 250 mg of Compound A, or a pharmaceutically acceptable salt thereof, on a free acid equivalent basis, and a pharmaceutically acceptable stabilizing polymer, or combination of pharmaceutically acceptable stabilizing polymers, and wherein the oral dosage form when administered as a single dose to a population of human subjects provides an average $C_{max}$ value that is less than about 1200 ng/mL for the population of human subjects. In one aspect, the oral dosage form when administered as a single dose to a population of human subjects provides an average $C_{max}$ value that is less than about 1000 ng/mL for the population of human subjects. In another aspect, the oral dosage form when administered as a single dose to a population of human subjects provides an average $C_{max}$ value from about 500 ng/mL to about 1200 ng/mL for the population of human subjects.

In another embodiment, the present disclosure relates to pharmaceutical compositions that are oral dosage forms comprising about 250 mg of Compound A, or a pharmaceutically acceptable salt thereof, on a free acid equivalent basis, and a pharmaceutically acceptable stabilizing polymer, or combination of pharmaceutically acceptable stabilizing polymers, and wherein the oral dosage form when administered as a single dose to a population of human subjects provides an average $AUC_{24}$ value that is at least about 4500 ng·hr/mL and an average $C_{max}$ value that is less than about 1200 ng/mL for the population of human subjects. In one aspect, the oral dosage form when administered as a single dose to a population of human subjects provides an average $AUC_{24}$ value from about 4500 ng·hr/mL to about 9000 ng·hr/mL and an average $C_{max}$ value from about 500 ng/mL to about 1200 ng/mL for the population of human subjects.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein:

the oral dosage form has a weight less than about 1500 mg;

the oral dosage form comprises Compound A, or a salt thereof, in an amount of about 225 mg to about 275 mg on a free acid equivalent weight basis; and the oral dosage form comprises the stabilizing polymer, or combination of stabilizing polymers, in an amount of at least about 5% by weight of the oral dosage form.

In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein:

the oral dosage form has a weight less than about 1500 mg;

the oral dosage form comprises Compound A, or a salt thereof, in an amount of about 240 mg to about 260 mg on a free acid equivalent weight basis; and the oral dosage form comprises the stabilizing polymer, or combination of stabilizing polymers, in an amount of at least about 10% by weight of the oral dosage form.

In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein:

the oral dosage form has a weight less than about 1500 mg;

the oral dosage form comprises Compound A, or a salt thereof, in an amount of about 240 mg to about 260 mg on a free acid equivalent weight basis; and the oral dosage form comprises the stabilizing polymer, or combination of stabilizing polymers, in an amount of about 10% to about 25% by weight of the oral dosage form.

In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein:

the oral dosage form has a weight less than about 1500 mg;

the oral dosage form comprises Compound A, or a salt thereof, in an amount of about 245 mg to about 255 mg on a free acid equivalent weight basis;

the oral dosage form comprises the stabilizing polymer, or combination of stabilizing polymers in an amount of at from about 10% to about 25% by weight of the oral dosage form; and the stabilizing polymer, or combination of stabilizing polymers, are selected from the group consisting of copovidone, polyvinylpyrrolidone, hydroxymethylpropylcellulose, SOLUPLUS®, and combinations thereof; wherein the hydroxymethylpropylcellulose has a viscosity less than about 100 centipoise in a 2% solution of at a temperature of about 20° C.

In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein:

the oral dosage form has a weight less than about 1500 mg;

the oral dosage form comprises Compound A, or a salt thereof, in an amount of about 245 mg to about 255 mg on a free acid equivalent weight basis;

the oral dosage form comprises the stabilizing polymer, or combination of stabilizing polymers in an amount of at from about 10% to about 25% by weight of the oral dosage form; and the stabilizing polymer, or combination of stabilizing polymers, comprises copovidone.

In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein:

the oral dosage form has a weight less than about 1500 mg;

the oral dosage form comprises Compound A, or a salt thereof, in an amount of about 240 mg to about 260 mg on a free acid equivalent weight basis; and the weight ratio of the stabilizing polymer, or combination of stabilizing polymers, to Compound A, or the salt thereof, on a free acid equivalent weight basis is from about 1:1 to about 1:4.

In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein:

the oral dosage form has a weight less than about 1500 mg;

the oral dosage form comprises Compound A, or a salt thereof, in an amount of about 245 mg to about 255 mg on a free acid equivalent weight basis;

the weight ratio of the stabilizing polymer, or combination of stabilizing polymers, to Compound A, or the salt thereof, on a free acid equivalent weight basis is from about 1:1 to about 1:4; and the stabilizing polymer, or combination of stabilizing polymers, is selected from the group consisting of copovidone, polyvinylpyrrolidone, hydroxymethylpropylcellulose, SOLUPLUS®, and combinations thereof; wherein the hydroxymethylpropylcellulose has a viscosity less than about 100 centipoise in a 2% solution of at a temperature of about 20° C.

In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to pharmaceutical compositions that are oral dosage forms comprising Compound A, or a pharmaceutically acceptable salt thereof, and a pharmaceutically acceptable stabilizing polymer, or combination of pharmaceutically acceptable stabilizing polymers, wherein:

the oral dosage form has a weight less than about 1500 mg;

the oral dosage form comprises Compound A, or a salt thereof, in an amount of about 245 mg to about 255 mg on a free acid equivalent weight basis;

the weight ratio of the stabilizing polymer, or combination of stabilizing polymers, to Compound A, or the salt thereof, on a free acid equivalent weight basis is from about 1:1 to about 1:4; and the stabilizing polymer, or combination of stabilizing polymers, comprises copovidone.

In one aspect, the oral dosage form has a weight less than about 1300 mg. In another aspect, the oral dosage form has a weight less than about 1100 mg. In another aspect, the oral dosage form has a weight less than about 1000 mg. In another aspect, the oral dosage form has a weight less than about 900 mg. In another aspect, the oral dosage form has a weight less than about 750 mg.

In another embodiment, the present disclosure relates to methods for treating hepatitis C in a subject in need of such treatment, wherein the method comprises administering to the subject a pharmaceutical composition comprising Compound A, or pharmaceutically acceptable salt thereof, and a pharmaceutically acceptable stabilizing polymer, or combination of pharmaceutically acceptable stabilizing polymers, as described in any of the above embodiments. In one aspect, the method further comprises administering to the subject one or more additional therapeutic agents. In another aspect, the pharmaceutical composition is an oral dosage form and is administered to the subject once daily. In another aspect, the pharmaceutical composition is an oral dosage form and is administered to the subject twice daily.

In another embodiment, the present disclosure relates to methods for preparing a pharmaceutical composition comprising Compound A, or a pharmaceutically acceptable salt thereof, wherein the method comprises preparing a pharmaceutical composition comprising (i) Compound A, or salt thereof, and (ii) a pharmaceutically acceptable stabilizing polymer, or combination of pharmaceutically acceptable stabilizing polymers, in an amount of about 5% to about 25% by weight of the pharmaceutical composition.

In another embodiment, the present disclosure relates to methods of improving tabletability of a pharmaceutical composition comprising Compound A, or a pharmaceutically acceptable salt thereof, wherein the method comprises preparing a pharmaceutical composition comprising (i) Compound A, or a salt thereof, and (ii) a pharmaceutically acceptable stabilizing polymer, or combination of pharmaceutically acceptable stabilizing polymers, in an amount of about 5% to about 25% by weight of the pharmaceutical composition.

In another embodiment, the present disclosure relates to methods of enhancing bioavailability of Compound A, or a pharmaceutically acceptable salt thereof, in a subject comprising:

preparing a pharmaceutical composition comprising Compound A, or a pharmaceutically acceptable salt thereof, and a pharmaceutically acceptable stabilizing polymer, or combination of pharmaceutically acceptable stabilizing polymers; and administering the pharmaceutical composition to the subject.

In one aspect, the bioavailability of Compound A, or the salt thereof, in the subject is enhanced by at least 30% relative to a similar pharmaceutical composition that does not comprise the stabilizing polymer, or combination of stabilizing polymers.

In another embodiment, the present disclosure relates to methods of reducing the amount of Compound A, or a pharmaceutically acceptable salt thereof, in a pharmaceutical composition necessary to achieve in a subject substantially the same bioavailability of Compound A, or a salt thereof, in the subject comprising:

preparing a pharmaceutical composition comprising Compound A, or a pharmaceutically acceptable salt thereof, and a pharmaceutically acceptable stabilizing polymer, or combination of pharmaceutically acceptable stabilizing polymers; and administering the pharmaceutical composition to the subject.

In one aspect, the amount of Compound A, or salt thereof, in said pharmaceutical composition is reduced by at least 30% relative to a substantially similar pharmaceutical composition that does not comprise comprising the stabilizing polymer, or combination of stabilizing polymers.

EXAMPLES

The following specific examples are illustrative and are not to be considered to limit the scope of the disclosure. All alternatives, modifications, and equivalents of the specific examples are included within the scope of the claims.

Example 1

Formulations 1-20

Table 2 presents non-limiting examples of the formulations described above. Compound A referenced in Table 2 below is the Compound A monosodium salt monohydrate and the corresponding weight percent is the free acid equivalent weight percent.

TABLE 2

FORMULATIONS C-1 AND 1-16

| | | Formulation | | | | | | | | |
|---|---|---|---|---|---|---|---|---|---|---|
| | Component | C-1 % w/w | 1 % w/w | 2 % w/w | 3 % w/w | 4 % w/w | 5 % w/w | 6 % w/w | 7 % w/w | 8 % w/w |
| Active Agent | Compound A | 40 | 40 | 40 | 40 | 40 | 40 | 40 | 40 | 40 |
| Disintegrant | Croscarmellose sodium | 5 | 5 | 5 | 5 | 5 | 5 | 5 | 5 | 5 |
| Filler | Lactose | 7.8 | 7 | 7 | 7 | 7 | 7 | 7 | 7 | 7 |
| | MCC-Avicel PH101 | 0 | 0 | 0 | 0 | 0 | 0 | 0 | 0 | 0 |
| | MCC-Avicel PH102 | 44.2 | 40 | 35 | 25 | 15 | 0 | 0 | 0 | 0 |
| | MCC-Avicel PH105 | 0 | 0 | 0 | 0 | 0 | 40 | 35 | 25 | 15 |
| | MCC-Avicel DG | 0 | 0 | 0 | 0 | 0 | 0 | 0 | 0 | 0 |
| Stabilizing Polymer | Kollidon ® VA 64 fine | 0 | 5 | 10 | 20 | 30 | 5 | 10 | 20 | 30 |
| | Kollidon ® VA 64 | 0 | 0 | 0 | 0 | 0 | 0 | 0 | 0 | 0 |
| Glidant (intra) | Colloidal SiO$_2$ | 1.0 | 1.0 | 1.0 | 1.0 | 1.0 | 1.0 | 1.0 | 1.0 | 1.0 |

TABLE 2-continued

FORMULATIONS C-1 AND 1-16

| | | | | | | | | | | |
|---|---|---|---|---|---|---|---|---|---|---|
| Glidant (entra) | Colloidal SiO$_2$ | 0 | 0 | 0 | 0 | 0 | 0 | 0 | 0 | 0 |
| Lubricant (intra) | Magnesium stearate | 0.4 | 0.4 | 0.4 | 0.4 | 0.4 | 0.4 | 0.4 | 0.4 | 0.4 |
| Lubricant (extra) | Magnesium stearate | 1.6 | 1.6 | 1.6 | 1.6 | 1.6 | 1.6 | 1.6 | 1.6 | 1.6 |
| | Total | 100 | 100 | 100 | 100 | 100 | 100 | 100 | 100 | 100 |

| | | Formulation | | | | | | | |
|---|---|---|---|---|---|---|---|---|---|
| | Component | 9 % w/w | 10 % w/w | 11 % w/w | 12 % w/w | 13 % w/w | 14 % w/w | 15 % w/w | 16 % w/w |
| Active Agent | Compound A | 40 | 40 | 40 | 40 | 40 | 40 | 40 | 40 |
| Disintegrant | Croscarmellose sodium | 5 | 5 | 5 | 5 | 5 | 5 | 5 | 5 |
| Filler | Lactose | 7 | 7 | 7 | 7 | 7 | 7 | 7 | 7 |
| | MCC-Avicel PH101 | 0 | 15.5 | 0 | 0 | 0 | 0 | 0 | 0 |
| | MCC-Avicel PH102 | 0 | 15.25 | 0 | 0 | 0 | 0 | 0 | 0 |
| | MCC-Avicel PH105 | 0 | 0 | 42.1 | 20.6 | 39.4 | 40.9 | 30.75 | 30.75 |
| | MCC-Avicel DG | 25 | 0 | 0 | 0 | 0 | 0 | 0 | 0 |
| Stabilizing Polymer | Kollidon ® VA 64 fine | 20 | 0 | 5 | 25 | 5 | 5 | 15 | 15 |
| | Kollidon ® VA 64 | 0 | 15 | 0 | 0 | 0 | 0 | 0 | 0 |
| Glidant (intra) | Colloidal SiO$_2$ | 1.0 | 0.6 | 0 | 0 | 1.2 | 1.2 | 0.6 | 0 |
| Glidant (entra) | Colloidal SiO$_2$ | 0 | 0 | 0 | 0 | 0 | 0 | 0 | 0.6 |
| Lubricant (intra) | Magnesium stearate | 0.4 | 0.4 | 0.4 | 0.4 | 0.4 | 0.4 | 0.4 | 0.4 |
| Lubricant (extra) | Magnesium stearate | 1.6 | 1.25 | 0.5 | 2.0 | 2.0 | 0.5 | 1.25 | 1.25 |
| | Total | 100 | 100 | 100 | 100 | 100 | 100 | 100 | 100 |

* MCC is microcrystalline cellulose.

Table 3 presents additional non-limiting examples of components of the disclosed formulations and their percentage by weight (w/w) of the formulation. Compound A referenced in Table 3 below is the Compound A monosodium salt monohydrate and the corresponding weight percent is the free acid equivalent weight percent.

TABLE 3

FORMULATIONS 17-20

| | | FORMULATION | | | |
|---|---|---|---|---|---|
| | COMPONENT | 17 % w/w | 18 % w/w | 19 % w/w | 20 % w/w |
| Intragranular | | | | | |
| Active Agent | Compound A | 40.0 | 40.0 | 40.0 | 40.0 |
| Disintegrant | Croscarmellose sodium | 5.0 | 5.0 | 5.0 | 5.0 |
| Filler | Lactose | 7.0 | 7.0 | 7.0 | 0 |
| | MCC*--Avicel 102 | 17.5 | 17.5 | 10.0 | 0 |
| Bioavailability enhancer | Kollidon ® VA 64 fine | 10.0 | 10.0 | 20.0 | 30.0 |
| Glidant | Colloidal SiO$_2$ | 1.0 | 1.0 | 1.0 | 0.5 |
| Lubricant | Magnesium stearate | 0.4 | 0.4 | 0.4 | 0.4 |
| Extragranular | | | | | |
| Filler | Lactose | 0 | 0 | 0 | 7.8 |
| | MCC*--Avicel PH 200 | 17.5 | 0 | 15.0 | 0 |
| | MCC*--Avicel PH102 | 0 | 17.2 | 0 | 14.2 |

TABLE 3-continued

FORMULATIONS 17-20

| | | FORMULATION | | | |
|---|---|---|---|---|---|
| | COMPONENT | 17 % w/w | 18 % w/w | 19 % w/w | 20 % w/w |
| Glidant | Colloidal SiO$_2$ | 0 | 0.3 | 0 | 0.5 |
| Lubricant | Magnesium stearate | 1.6 | 1.6 | 1.6 | 1.6 |
| | Total | 100 | 100 | 100 | 100 |

The exemplified formulations were prepared using blending, roller compaction and milling, tablet compression and tablet coating. The manufacturing process flow diagram is presented in FIG. 1.

In a first blending step; active agent, compound A; fillers, microcrystalline cellulose and lactose; bioavailability enhancer; disintegrant, croscarmellose sodium; and glidant, colloidal silicon dioxide; were combined, sieved, and blended.

After the first blending step, the blend that contains the active agent and all excipients except the lubricant was blended with 0.4% intragranular magnesium stearate. The lubricated blend was roller compacted using the Gerties Roller Compactor, installed with a smooth surface master roll that was coupled with a knurled surface slave roll. The resultant ribbons with solid fraction range of 0.55 to 0.75 were milled through a square mesh screen with aperture of 1.0 to 1.5 mm coupled with a star-shaped rotor, at a speed of 50-60 rpm. Prior to tablet compression, the granules were further lubricated with the remainder of magnesium stearate. For this final lubrication step, the amount of magnesium stearate was adjusted based on the yield of the roller compaction step. Subsequently, the lubricated granules are compressed into tablets using a rotary tablet press using pressure of 15-40KN with target tablet hardness of 18-35 KP or target tensile strength of 1.5-2.0 MPa. The compressed tablets were coated as needed. For example, formulation 10 was coated with Opadry II, and formulations 3 and 7 were coated with Kollicoat IR.

Prior to compression into tablets, the granules were lubricated with additional magnesium stearate prior to compression. The amount of magnesium stearate and extra-granular excipients were adjusted for blending as a function of the yield of the dry granulation step.

Following the final blending step, the final blend is compressed using a press under the same compression force to maintain similar hardness in the tablets.

Example 2

In Vitro Dissolution and In Vivo Dog Studies

Formulations A, B, C, and D

A. In Vitro Dissolution Studies

An in vitro dissolution study was conducted as an initial assessment of predicted bioavailability in vivo of 400 mg tablets with and without bioavailability enhancing agent. Table 4 lists the formulations of Reference A and Test Formulations B, C and D (which are identical to Formulations C-1, 15, 7, and 12 of Table 2, respectively). The Reference A formulation did not contain a bioavailability enhancer in contrast to Test Formulations B, C and D which each contain about 15, 20 and 25 percent w/w of a bioavailability enhancer, respectively. Compound A referenced in Table 4 below is the Compound A monosodium salt monohydrate and the corresponding weight percent is the free acid equivalent weight percent.

TABLE 4

FORMULATIONS A-D

| Ingredient | Reference A | Test Formulation B | Test Formulation C | Test Formulation D |
|---|---|---|---|---|
| | %, w/w | | | |
| Compound A (Na Salt) | 40* | 40* | 40** | 40* |
| Avicel PH 105 | — | 30.75 | 25 | 21 |
| Avicel PH 102 | 44.2 | — | — | — |
| Kollidon VA64 Fine | — | 15 | 20 | 25 |
| Lactose, Monohydrate | 7.8 | 7.0 | 7.0 | 7.0 |
| Sodium Croscarmellose | 5.0 | 5.0 | 5.0 | 5.0 |
| Colloidal Silicon Dioxide | 1.0 | 0.6 | 1.0 | 0 |
| Mg Stearate | 2.0 | 1.65 | 2.0 | 2.0 |
| Total tablet weight | 1060 mg | 1060 mg | 1060 mg | 1060 mg |

*API particle size of D50 = 40 um
**API particle size D50 = 80 um

Two types of dissolution tests were applied to evaluate the dissolution profile of these tablets.

1. QC Dissolution Test

Figure 5:
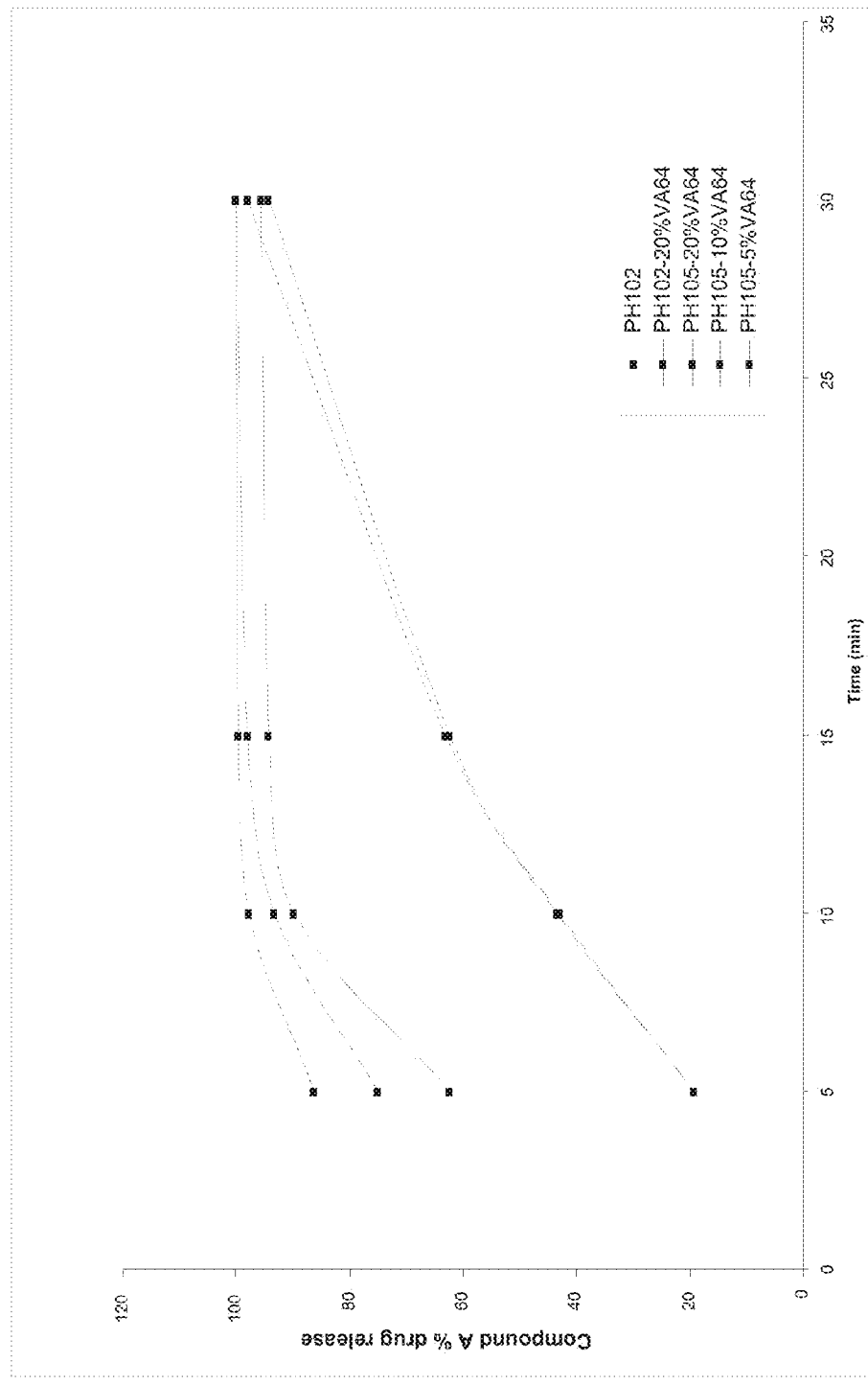
FIG. 5 In vitro dissolution profiles of Reference Formulation C-1 and Formulations 3, 5, 6 and 7.

FIG. 5 shows dissolution profiles obtained from a QC dissolution test under a sink condition. The dissolution medium contained 0.05 M sodium phosphate and 0.25 mM cTAB and was maintained at a pH of 6.8. The dissolution testing was conducted using USP dissolution Apparatus 2 (paddle) operating at 75 RPM at 37±0.5° C. Samples from the dissolution medium were pulled from the aqueous phase at predetermined time points and assayed by HPLC. It is apparent that a small decrease of the drug release % was accompanied by the addition of 5% bioavailability enhancing agents (e.g., VA 64) within 30 minutes. A significantly greater reduction of the drug release % at t=15 min is observed with 20% VA64 in the formulation. This indicates that the presence of the bioavailability enhancing agent decreases the dissolution rate of the drug as revealed by the conventional USP II dissolution test.

2. Biphasic Dissolution Test

Figure 2:
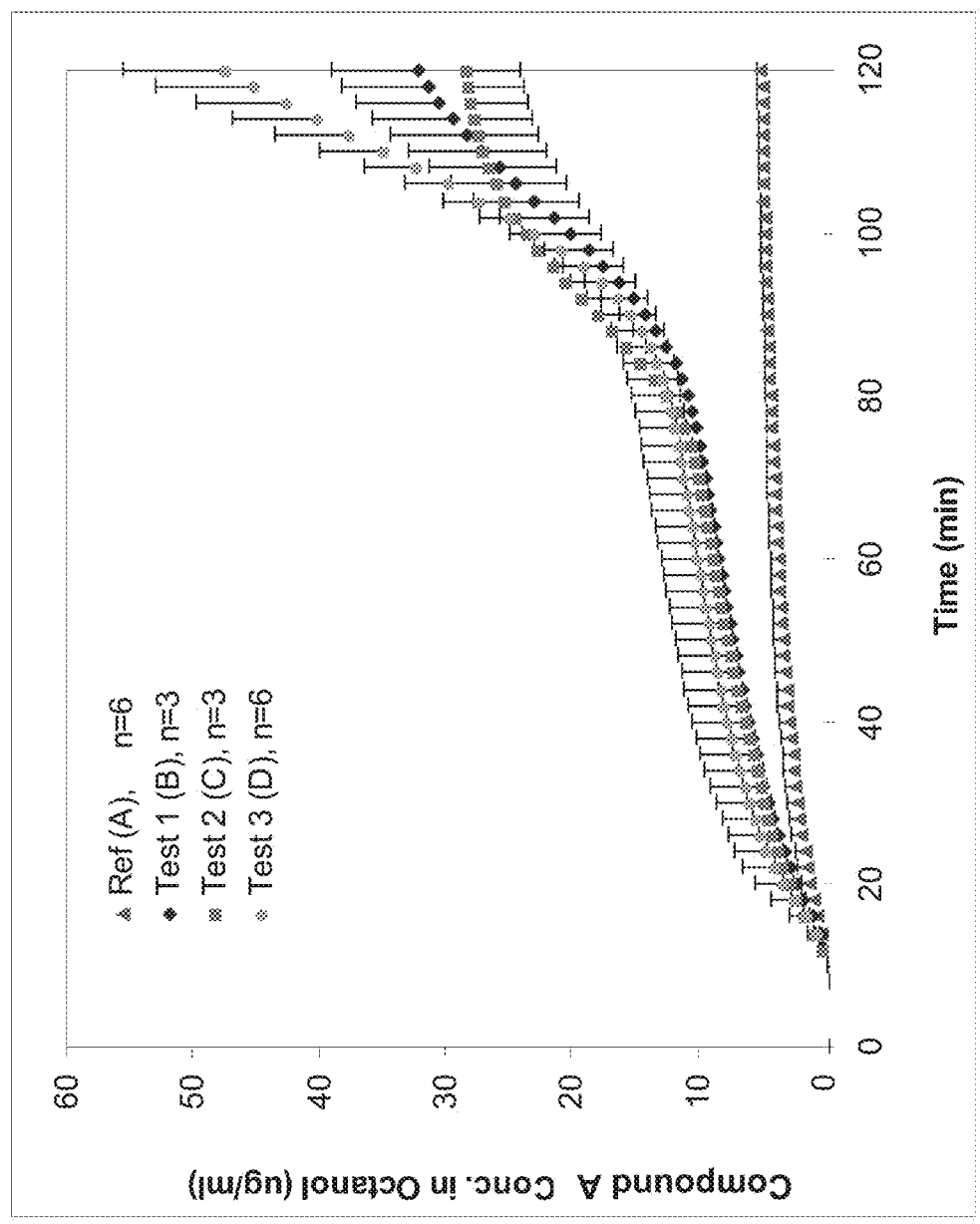
FIG. 2 Dissolution of selected roller compaction tablets.

Another dissolution test, referred to as a biphasic dissolution test, consists of an aqueous phase and organic phase in a 100 mL glass vessel as described in FIG. 2. The aqueous phase was 40 mL of 80 mM phosphate buffer (pH 6.8) and the organic phase was 30 mL of Octanol. Both phases were saturated with each other by mixing the aqueous phase with the Octanol phase under adequate agitation for 30 minutes prior to use. The aqueous phase was circulated between the USP IV flow cell and the vessel with a peristaltic pump. A dual paddle consisting of an additional paddle mounted on the regular compendial paddle was used in order to achieve sufficient mixing in both aqueous and organic phases. The water bath for the vessels containing aqueous and organic phases and USP IV flow cells were maintained at 37±0.2° C.

In order to mimic in vivo dosing environment in dogs, a tablet was put into a flow cell containing 10 mL of 0.01N HCl solution. The flow cell was placed into a horizontal shaker (Orbit Environ Shaker) set up at 150 rpm in a 37° C. After 30 minutes shaking, the flow cell was taken out and put into a Sotax CP7 USP Apparatus 4 unit. The contents in the flow cell were pumped into the 40 mL of 80 mM phosphate buffer (pH 6.8) aqueous phase. The drug dissolved in the aqueous phase partitions into the octanol phase. The UV absorbance in the octanol phase was measured every two minutes by using a UV probe (PION µDISS Profile).

Figure 3:
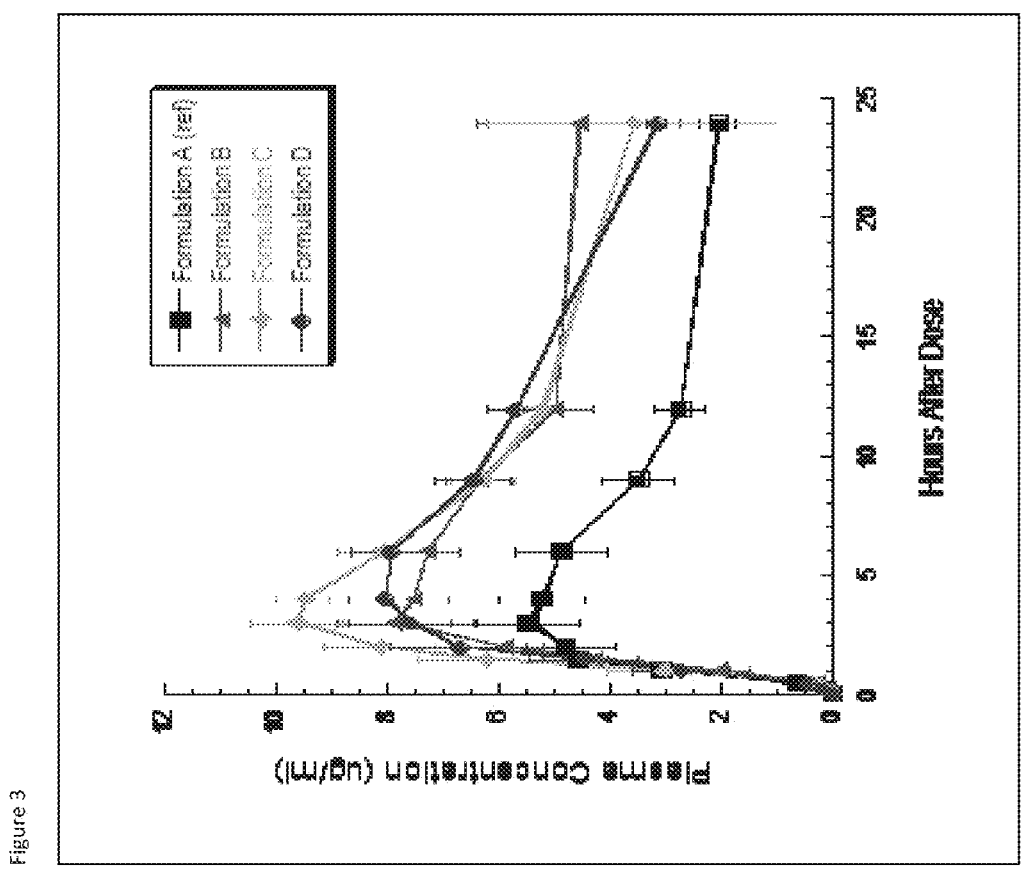
FIG. 3 Pharmacokinetic profiles of Formulations A, B, C and D.

The drug concentration-time profiles obtained from the biphasic system are illustrated in FIG. 3. According to FIG. 2, within 120 minutes each of the formulations containing the bioavailability enhancing agent had achieved four times higher mean concentration than the reference formulation without the bioavailability enhancing agent.

B. In Vivo Dog Study

The Reference A formulation and Test Formulations B, C and D of the in vitro dissolution test described above were also tested in dogs to evaluate their bioavailability and to establish an in vitro-in vivo relationship (IVIVR) between the biphasic dissolution profiles and their bioavailability.

A single group of six dogs received a 400 mg dose of each formulation in 5 dosing periods. The dogs were fasted overnight prior to dosing, and each dog was pre-treated with histamine about 30 minutes prior to dosing. Food was provided 4 hours after drug administration. A period of one week was allowed for washout between each of the dosing periods. Studies were conducted in dogs to compare the Compound A plasma concentrations obtained from the experimental formulations. The studies were conducted using a sequential design in a single group of six beagle dogs. The dogs were fasted overnight prior to dosing. Approximately 30 minutes prior to drug administration, each dog received a 100 µg/kg subcutaneous dose of histamine. Food was returned after the 4 hour sampling time point; animals were permitted free access to water. Blood samples for plasma analysis were obtained from each dog 0.25, 0.5, 1, 1.5, 2, 3, 4, 6, 9, 12, 15 and 24 hours after dosing. Plasma concentrations of Compound A were determined by HPLC-MS/MS. A washout period of at least one week separated the dosing periods.

The bioavailability study results for the 400 mg tablets in dogs are listed in Table 5 and shown in FIG. 3.

TABLE 5

BIOAVAILABILITY STUDY RESULTS

| 400 mg/dog | $C_{max}$ | $T_{max}$ | $AUC_{0-t}$ | Pt. Estimate $C_{max}$ | AUC |
|---|---|---|---|---|---|
| Reference A | 5.69 (0.86) | 3.0 (0.8) | 76.3 (11.7) | | |
| Test Formulation B | 8.09 (0.90) | 4.0 (0.5) | 119.4 (20.4) | 1.4 | 1.5 |
| Test Formulation C | 10.16 (0.64) | 3.4 (0.2) | 124.5 (14.4) | 1.8 | 1.6 |
| Test Formulation D | 8.88 (0.74) | 3.8 (0.7) | 129.2 (10.4) | 1.6 | 1.7 |

Mean (SEM, n = 5);
$C_{max}$ [µg/mL];
$T_{max}$ [hr];
$AUC_{0-t}$ [µg · hr/mL]

All three test formulations containing a bioavailability enhancing agent provided significantly higher $C_{max}$ and AUC of Compound A than the Reference formulation.

The data also confirms that the bioavailability of the test formulations is insensitive to the variation of API particle size at least within a range of $D_{50}$ between 40 to 80 µm. In particular, Test Formulation C having an API particle size of $D_{50}$=80 µm shows comparable exposure as compared to the Test formulation B having an API particle size of $D_{50}$=40 µm.

Figure 4:
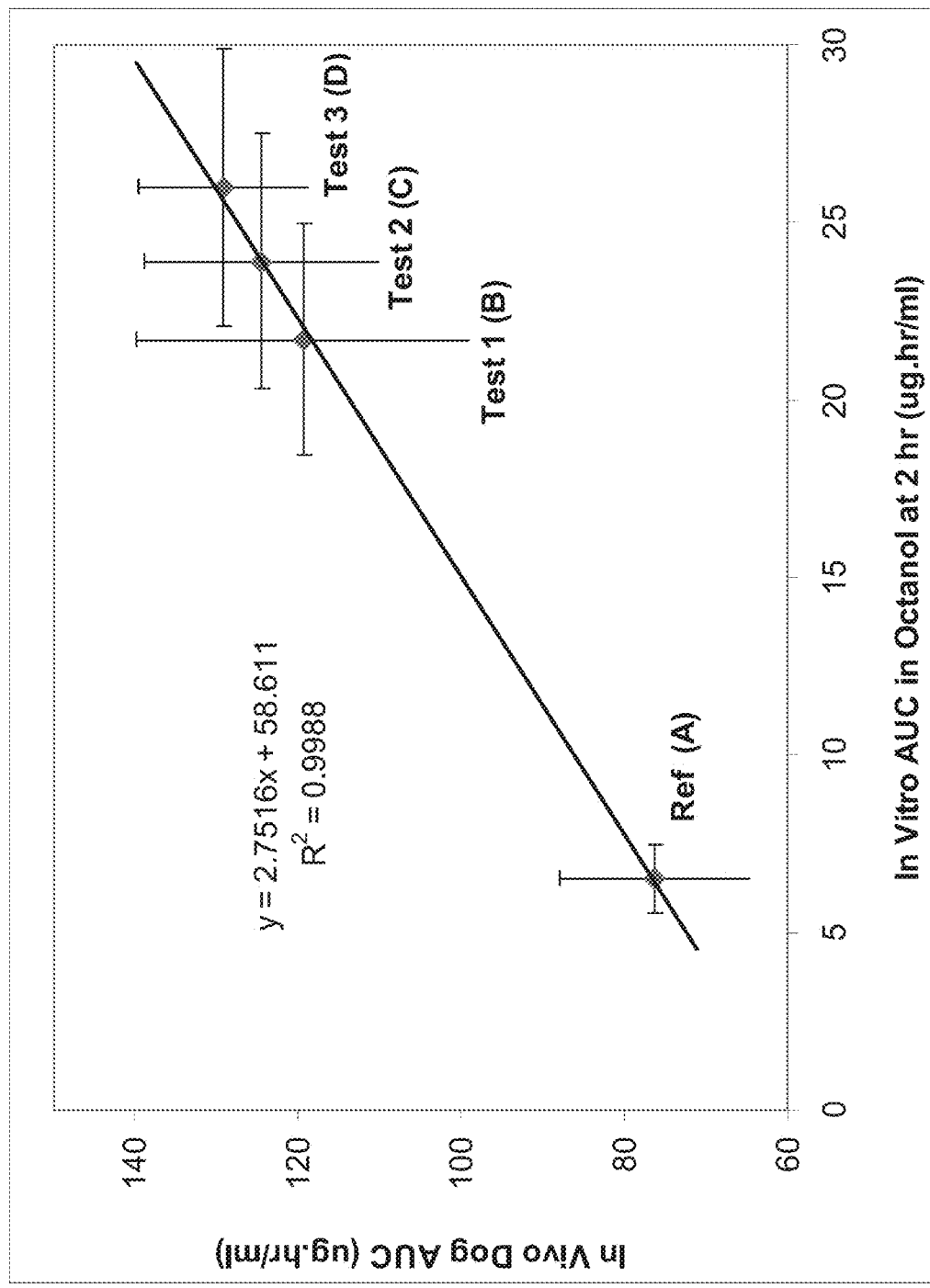
FIG. 4 Correlation of in vitro and in vivo AUCs of Formulations A, B, C and D.

As illustrated in FIG. 4, the in vitro AUCs of the concentration-time profile from these formulations in octanol between t=0 and t=120 min. are found to be proportional to the mean values of AUC and $C_{max}$ of the tested formulations in vivo. Accordingly, the IVIVR obtained by this study indicates that the biphasic test provides good predictability of bioavailability in vivo.

Example 3

In Vitro Dissolution and In Vivo Dog Studies

Formulations 3, 5, 6, and 7

As set forth in Table 6 below, Formulations C-1, 3, 5, 6 and 7 using the Compound A monosodium salt monohydrate were also tested for various parameters of in vitro dissolution and in vivo bioavailability in dogs.

TABLE 6

FORMULATIONS C-1, 3, 5, 6, AND 7

| | Formulations | | | | |
|---|---|---|---|---|---|
| | Reference C-1 | Formulation 3 | Formulation 5 | Formulation 6 | Formulation 7 |
| | Unit Dose, Compound A monosodium salt monohydrate[a] | | | | |
| Component | 200 mg % w/w | 200 mg % w/w | 200 mg % w/w | 200 mg % w/w | 200 mg % w/w |
| Compound A monosodium salt monohydrate | 40.0 | 40.0 | 40.0 | 40.0 | 40.0 |
| Microcrystalline Cellulose (Avicel PH 105) | — | — | 40.0 | 35.0 | 25.0 |
| Microcrystalline Cellulose (Avicel PH 102) | 44.2 | 25.0 | — | — | — |
| Lactose monohydrate, Fast flo (#316) | 7.8 | 7.0 | 7.0 | 7.0 | 7.0 |
| Kollidon VA64 | — | 20.0 | 5.0 | 10.0 | 20.0 |
| Croscarmellose, Sodium | 5.0 | 5.0 | 5.0 | 5.0 | 5.0 |
| Colloidal Silicon Dioxide | 1.0 | 1.0 | 1.0 | 1.0 | 1.0 |
| Magnesium Stearate | 2.0 | 2.0 | 2.0 | 2.0 | 2.0 |
| Total | 100.0 | 100.0 | 100.0 | 100.0 | 100.0 |

[a]Unit dose and w/w % based on free acid equivalent amount of Compound A.

A. In Vitro Dissolution Study

In vitro dissolution results are shown in FIG. 5.

B. In Vivo Dog Study

A single group of six dogs received a 200 mg dose of each formulation in 5 dosing periods. The dogs were fasted overnight prior to dosing, and each dog was pre-treated with histamine about 30 minutes prior to dosing. Food was provided 4 hours after drug administration. A period of one week was allowed for washout between each of the dosing periods. Studies were conducted in dogs to compare the Compound A plasma concentrations obtained from the experimental formulations. The studies were conducted using a sequential design in a single group of six beagle dogs. The dogs were fasted overnight prior to dosing. Approximately 30 minutes prior to drug administration, each dog received a 100 µg/kg subcutaneous dose of histamine. Food was returned after the 4 hour sampling time point; animals were permitted free access to water. Blood samples for plasma analysis were obtained from each dog 0.25, 0.5, 1, 1.5, 2, 3, 4, 6, 9, 12, 15 and 24 hours after dosing. Plasma concentrations of Compound A were determined by HPLC-MS/MS. A washout period of at least one week separated the dosing periods.

Table 7 presents data from in vivo bioavailability testing in dogs of formulations 3, 5, 6 and 7 indicating favorable levels of Compound A in vivo.

TABLE 7

IN VIVO STUDY RESULTS

| 200 mg Oral Dose | | Point Estimates | |
|---|---|---|---|
| | $C_{max}$ | $T_{max}$ | $AUC_{0-24}$ |
| Formulation 3 | 5.66 (0.87) | 6.5 (3.5) | 96.20 (18.79) |
| Formulation 5 | 6.10 (1.00) | 3.8 (0.5) | 106.84 (21.36) |
| Formulation 6 | 6.22 (0.81) | 5.0 (1.3) | 97.19 (14.21) |

TABLE 7-continued

IN VIVO STUDY RESULTS

| 200 mg Oral | | Point Estimates | |
|---|---|---|---|
| Dose | $C_{max}$ | $T_{max}$ | $AUC_{0-24}$ |
| Formulation 7 | 7.85 (0.67) | 7.8 (1.3) | 105.54 (13.96) |
| Reference C-1 | 4.86 (0.86) | 3.7 (0.6) | 73.09 (12.42) |

Mean (SEM, n = 6);
$C_{max}$ [µg/mL];
$T_{max}$ [hours];
$AUC_{0-24}$ [µg · hour/mL].

The plasma drug concentration of each sample was calculated by least squares linear regression analysis of the peak area ratio of the spiked plasma standards versus concentration for each compound. The maximum plasma concentration ($C_{max}$) and the time to reach the maximum plasma concentration ($T_{max}$) were read directly from the observed concentration-time data. The plasma concentration data were submitted to multi-exponential curve fitting using WinNonlin to obtain estimates of pharmacokinetic parameters. The area under the plasma concentration-time curve from 0 to t hours (time of the last measurable plasma concentration) after dosing ($AUC_t$) was calculated using the linear trapezoidal rule. The residual area extrapolated to infinity, determined as the final measured plasma concentration (CO divided by the terminal elimination rate constant (b), was added to $AUC_t$ to produce the total area under the curve ($AUC_\infty$). Point estimates for $C_{max}$ and $AUC_{0-24}$ were calculated from the test formulations vs. reference formulation; the reported point estimate was calculated from a mean of the log-transformed values. As illustrated in Table 7, formulations 3, 5, 6 and 7 improved AUC over the control, C-1, by more than 30%.

Example 4

In Vivo Human Study

Formulations T-1, T-2, and T-3

Three pharmaceutical compositions of comprising Compound A monosodium salt monohydrate were prepared in accordance with the formulations set forth in Table 8.

TABLE 8

FORMULATIONS R-1, T-1, T-2, AND T-3

| | Formulations | | | |
|---|---|---|---|---|
| | R-1 | T-1 | T-2 | T-3 |
| | Unit Dose, Compound A monosodium salt monohydrate[a] | | | |
| Component | 400 mg | 400 mg | 300 mg | 250 mg |
| | % w/w | | | |
| Compound A monosodium salt monohydrate | 40.0 | 40.0 | 40.0 | 40.0 |
| Microcrystalline Cellulose (Avicel PH 101) | — | 15.5 | 15.5 | 15.5 |
| Microcrystalline Cellulose (Avicel PH 102) | 44.2 | 15.3 | 15.3 | 15.3 |
| Lactose monohydrate, Fast flo (#316) | 7.8 | 7.0 | 7.0 | 7.0 |
| Kollidon VA64 | — | 15.0 | 15.0 | 15.0 |
| Croscarmellose, Sodium | 5.0 | 5.0 | 5.0 | 5.0 |
| Colloidal Silicon Dioxide | 1.0 | 0.6 | 0.6 | 0.6 |
| Magnesium Stearate | 2.0 | 1.6 | 1.6 | 1.6 |
| Total | 100.0 | 100.0 | 100.0 | 100.0 |

[a]Unit dose and w/w % based on free acid equivalent amount of Compound A.

The Formulation R-1 is a 400 mg tablet that does not contain a bioavailability enhancer in contrast to Formulations T-1, T-2 and T-3 which each comprise about 15 percent w/w of a bioavailability enhancer. Formulation T-1 is a 400 mg tablet, Formulation T-2 is a 300 mg tablet, and Formulation T-3 is a 250 mg tablet.

Formulation R-1 and Formulations T-1 and T-2 were initially dosed in 18 healthy human subjects. Doses were taken in two 7-day periods separated by 7 days. Each dose of study drug was taken orally with approximately 240 mL of water approximately 30 minutes after the start of a moderate-fat breakfast.

Figure 6:
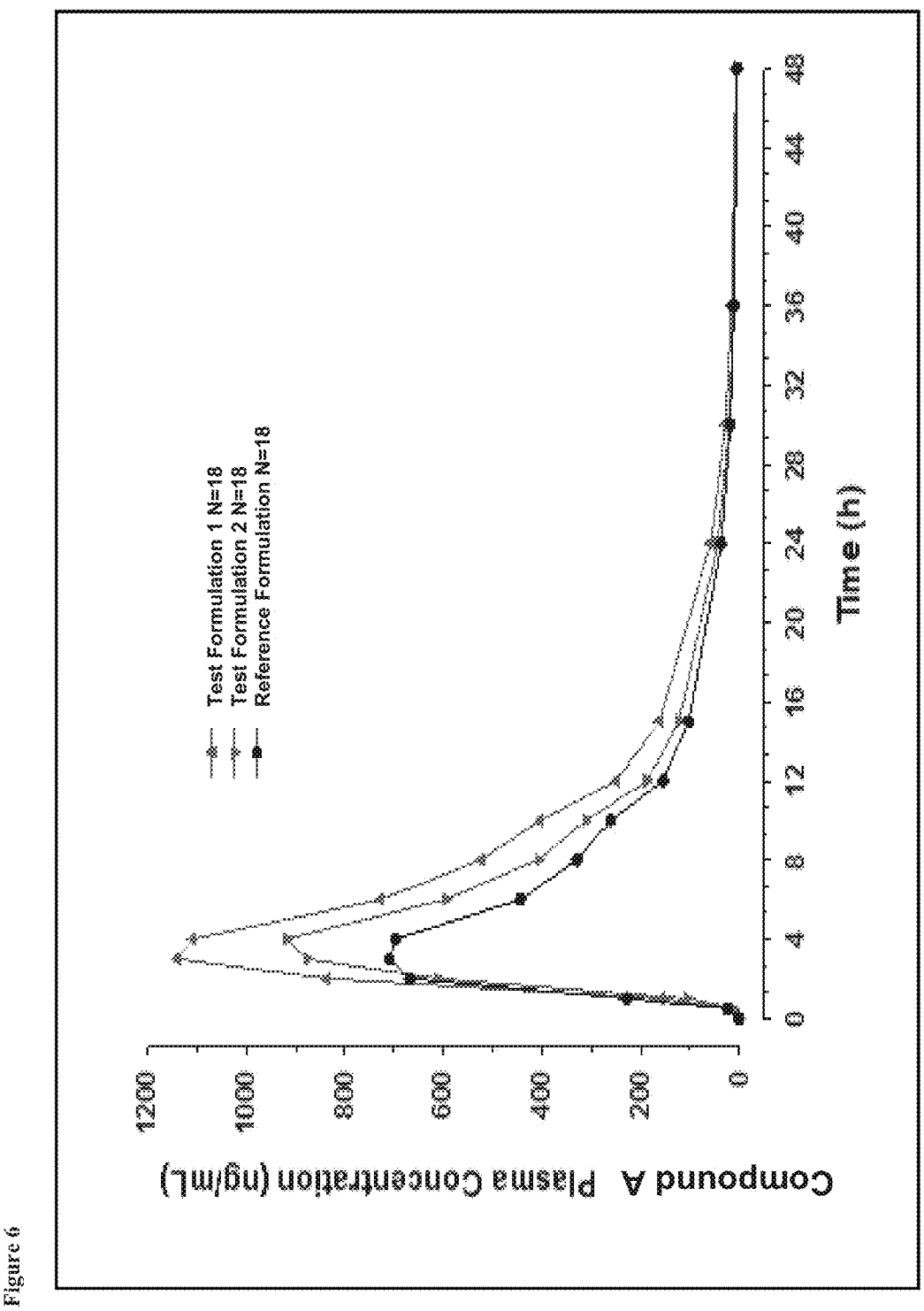
FIG. 6 Pharmacokinetic profiles of Formulations R-1, T-1, and T-2.

FIG. 6 illustrates the pharmacokinetic profiles of Formulation R-1 and Formulations T-1 and T-2 showing that the test formulations having a bioavailability enhancing agent achieved at least a 30% higher peak plasma concentration than the Reference formulation.

Table 9 presents the data comparing mean pharmacokinetic parameters of Formulation T-1 and Formulation T-2 with those of the Formulation R-1.

TABLE 9

IN VIVO DATA (FORMULATIONS R-1, T-1, AND T-2)

| PK Parameter | | R-1 (% CV) | Ratio (90% C.I.)[a] |
|---|---|---|---|
| | T-1 (% CV) | | |
| $C_{max}$ | 1240 (43) | 800 (38) | 1.48 (1.29-1.71) |
| $AUC_\infty$ | 9510 (39) | 6200 (42) | 1.53 (1.38-1.69) |
| | T-2 (% CV) | | |
| $C_{max}$ | 1020 (47) | 800 (38) | 1.25 (1.09-1.45) |
| $AUC_\infty$ | 7400 (41) | 6200 (42) | 1.19 (1.08-1.32) |

[a]Antilogarithm of the difference (test minus reference) of the least squares means for logarithms The bioavailability results revealed that the T-1 tablet provided about 53% higher exposure of Compound A than that of the R-1 tablet. The bioavailability results also show that the T-2 tablet provided about 19% higher exposure of Compound A than that of the R-1 tablet, even at a 25% reduction in dose load.

An additional human pharmacokinetic study was performed in adult male subjects (N=8). Each subject received one T-1 tablet, followed by a single dose of 84 to 85 µg $^{14}$C-Compound A (nominal dose of 100 µg) containing not more than 10 kBq (270nCi) from an IV solution formulation over 15 minutes, 2 hours and 45 minutes after administration of the tablet. The point estimates indicate that bioavailability of Compound A from a T-1 tablet is approximately 46% when compared to Compound A 84 to 85 µg administered as a short IV infusion. Based on this bioavailability study, the absolute bioavailability of Compound A from T-3 tablet is estimated to be about 70%.

Based on these results, a 250 mg tablet (Formulation T-3) tablet which includes about 15 percent w/w of a bioavailability enhancer was prepared and compared to the R-1 tablet in 32 healthy adult subjects to evaluate the bioavailability of the tablets. Subjects were divided into two sequence groups of 16 subjects in each group. During the first of two 7-day periods, the subjects in the first group were administered Formulation R-1 and the subjects in the second group were administered Formulation T-3. During the second period, the subjects in the first group were administered the Formulation T-3 and the subjects in the second group were administered Formulation R-1. The two periods were separated by 7 days. Each dose of study drug was taken orally with approximately 240 mL of water approximately 30 minutes after the start of a moderate-fat breakfast.

Figure 7:
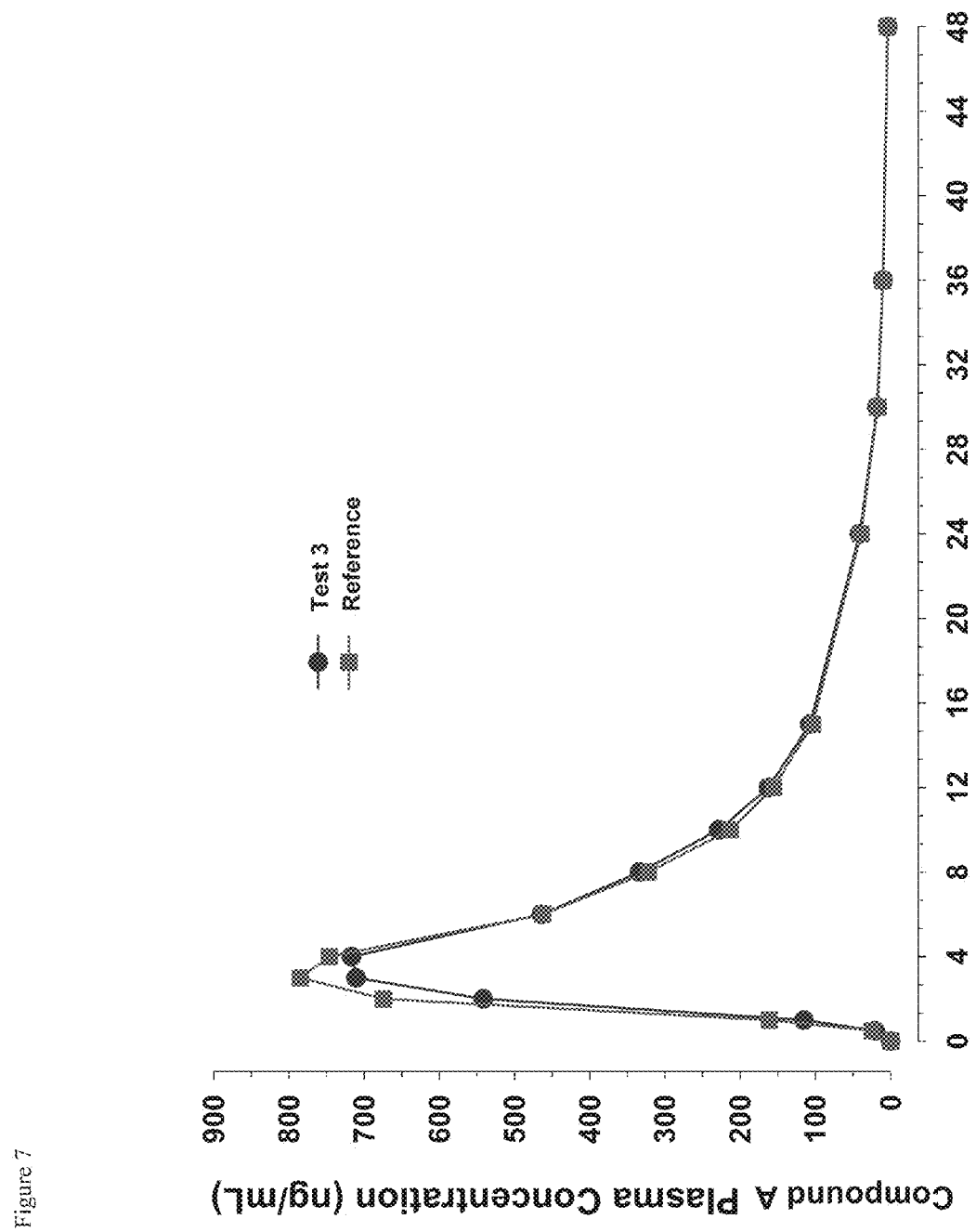
FIG. 7 Pharmacokinetic profiles of Formulations R-1 and T-3.

Table 10 and FIG. 7 present the data comparing the mean pharmacokinetic parameters of Formulation T-3 and Formulation R-1.

TABLE 10

IN VIVO DATA (FORMULATION T-3)

| PK Parameter | T-3 (250 mg) (% CV) | R-1 (400 mg) (% CV) | Ratio (90% C.I.)[b] |
|---|---|---|---|
| Compound A | | | |
| $C_{max}$ | 762 (41) | 847 (31) | 0.900 (0.820-0.987) |
| $AUC_\infty$ | 5800 (37) | 6060 (28) | 0.957 (0.893-1.025) |
| Compound A M1 Metabolite | | | |
| $C_{max}$ | 268 (41) | 290 (36) | 0.921 (0.853-0.996) |
| $AUC_\infty$ | 2000 (44) | 2140 (36) | 0.935 (0.880-0.992) |

Figure 8:
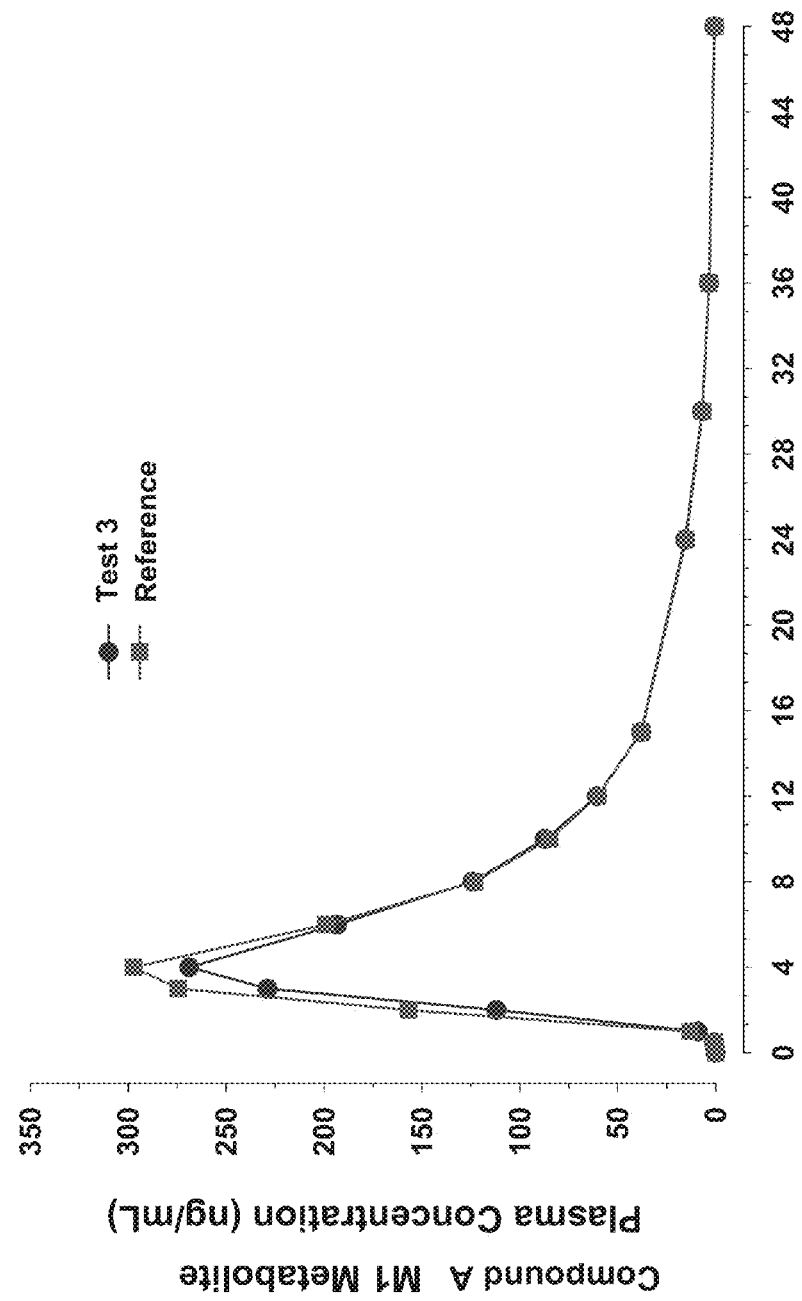
FIG. 8 Pharmacokinetic profiles of Formulation R-1 and Compound A M1 Metabolite from Formulation T-3
FIG. 9 Schematic diagram of a pH-dilution dissolution test system employed in Example 5.

[b]Antilogarithm of the difference (test minus reference) of the least squares means for logarithms As illustrated in Table 8 and FIGS. 7 and 8, Formulation T-3 (250 mg/table strength) shows the same AUC and $C_{max}$ as compared to the Formulation R-1 (400 mg/tablet strength).

Table 11 reports additional pharmacokinetic data obtained from another in vivo study involving Formulation T-3 and Formulation R-1.

TABLE 11

ADDITIONAL IN VIVO DATA (FORMULATION T-3)

| Pharmacokinetic Parameter | Units | Formulation T-3 (N = 32) | Formulation R-1 (N = 32) |
|---|---|---|---|
| COMPOUND A | | | |
| $C_{max}$ | ng/mL | 818 (41) | 887 (31) |
| $T_{max}$ | h | 3.47 (28) | 2.94 (27) |
| $t_{1/2}{}^a$ | h | 7.66 (20) | 7.44 (18) |
| $AUC_t$ | ng · h/mL | 6060 (37) | 6230 (28) |
| $AUC_{inf}$ | ng · h/mL | 6100 (37) | 6280 (28) |
| COMPOUND A METABOLITE | | | |
| $C_{max}$ | ng/mL | 288 (41) | 310 (36) |
| $T_{max}$ | h | 4.13 (50) | 3.69 (22) |

TABLE 11-continued

ADDITIONAL IN VIVO DATA (FORMULATION T-3)

| Pharmacokinetic Parameter | Units | Formulation T-3 (N = 32) | Formulation R-1 (N = 32) |
|---|---|---|---|
| $t_{1/2}{}^a$ | h | 5.99 (12) | 6.08 (13) |
| $AUC_t$ | ng · h/mL | 2120 (45) | 2250 (37) |
| $AUC_{inf}$ | ng · h/mL | 2140 (44) | 2280 (36) |

[a]Harmonic mean (pseudo-CV %)

Example 5

In Vitro Dissolution Study (pH Dilution)

Formulations R-1 and T-3

An in vitro dissolution study was conducted to evaluate Formulation R-1 and Formulation T-3. The study was designed to estimate formulation dependent in-vivo apparent solubility versus time across the gastrointestinal lumen by simulating physiologically relevant gastrointestinal transit processes (including pH, residence times, fluid volumes/dilutions). The compositions of the two formulations tested are shown in Table 12 below.

TABLE 12

FORMULATIONS R-1 AND T-3

| | FORMULATIONS | |
|---|---|---|
| | FORMULATION R-1 | FORMULATION T-3 |
| | Compound A monosodium salt monohydrate[a] | |
| | 400 mg | 250 mg |
| COMPONENT | % w/w | |
| Compound A monosodium salt monohydrate[a] | 40.0 | 40.0 |
| Microcrystalline Cellulose (Avicel PH 101) | — | 15.5 |
| Microcrystalline Cellulose (Avicel PH 102) | 44.2 | 15.3 |
| Lactose monohydrate, Fast flo (#316) | 7.8 | 7.0 |
| Kollidon VA64 | — | 15.0 |
| Croscarmellose, Sodium | 5.0 | 5.0 |
| Colloidal Silicon Dioxide | 1.0 | 0.6 |
| Magnesium Stearate | 2.0 | 1.6 |
| Total | 100.0 | 100.0 |

[a]Unit dose and w/w % based on free acid equivalent amount of Compound A.

Figure 9:
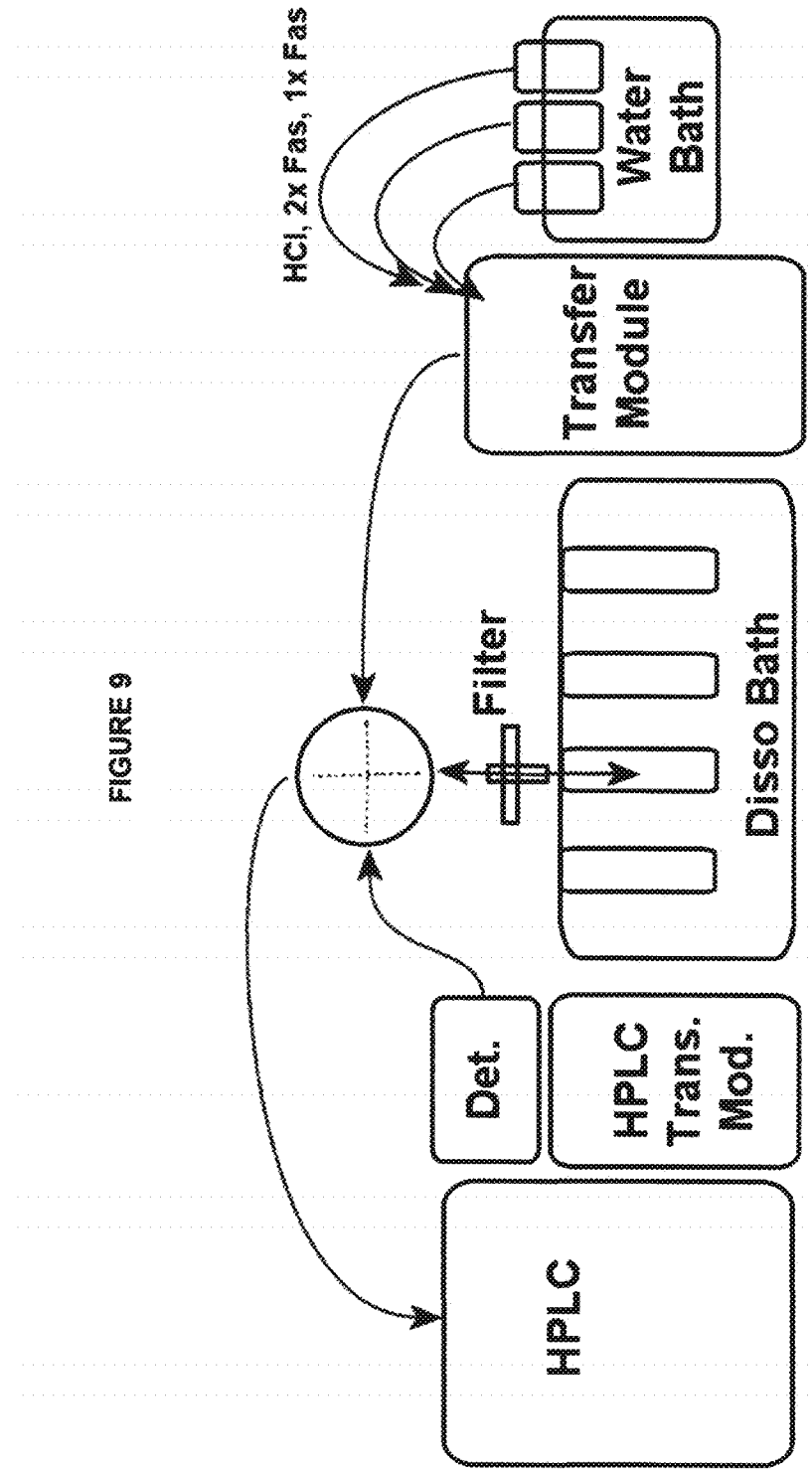

The study employed the pH-dilution instrumentation shown FIG. 9. This instrumentation included: (1) a Hanson Autoplus Maximizer transfer module to pump media into the dissolution vessels, (2) a Hanson SR8Plus dissolution station, and (3) a Waters 2695D Dissolution Alliance HPLC System.

The test duration was about 2.5 hours. The testing protocol is outlined in Table 13 below.

TABLE 13 pH-DILUTION DISSOLUTION PROTOCOL

DISSOLUTION CONDITIONS

1. Hanson 200 mL dissolution vessel.
2. Hanson USP Apparatus 1 basket s(10 mesh).
3. Fast simulated intestinal fluid (FaSSIF) medium and bath at 37° C.
4. 200 rpm.

INITIAL TASKS

1. Add pill to vessel basket (dry).
2. Turn on shaft rotation.
3. Transfer module pumps 30 mL of 0.01N HCl to each vessel.
4. Each vessel is held at acidic condition for 30 minutes.
5. Transfer module then pumps 30 mL of 2X FaSSIF to each vessel.
6. Each Vessel held at the new FaSSIF condition for 30 minutes.

SAMPLING TASKS

1. The Waters system rinses the transfer lines (4 × 2 mL) at each pull and returns the sample back through the filter membrane as a filter wash.
2. The Waters system then pulls/filters 2 mL from the dissolution vessel, transfers 200 µL of sample from each vessel at each designated time point into individual LC total recovery vials. The remaining sample returns to through the filter membrane to its designated dissolution vessel.
3. LC analysis begins immediately after first pull.
4. The transfer module adds 10 mL of 1x FaSSIF to the vessels.
5. Each vessel is held at the new FaSSIF condition for 20 min.
6. Sampling is repeated (step 1) for duration of study.
7. Time points begin after the 2X FaSSIF additions following the 30 minutes in 0.01N HCl. Time points collected are: t = 0, 20, 40, 60, 100, 140, 180, 300 minutes.

Figure 10:
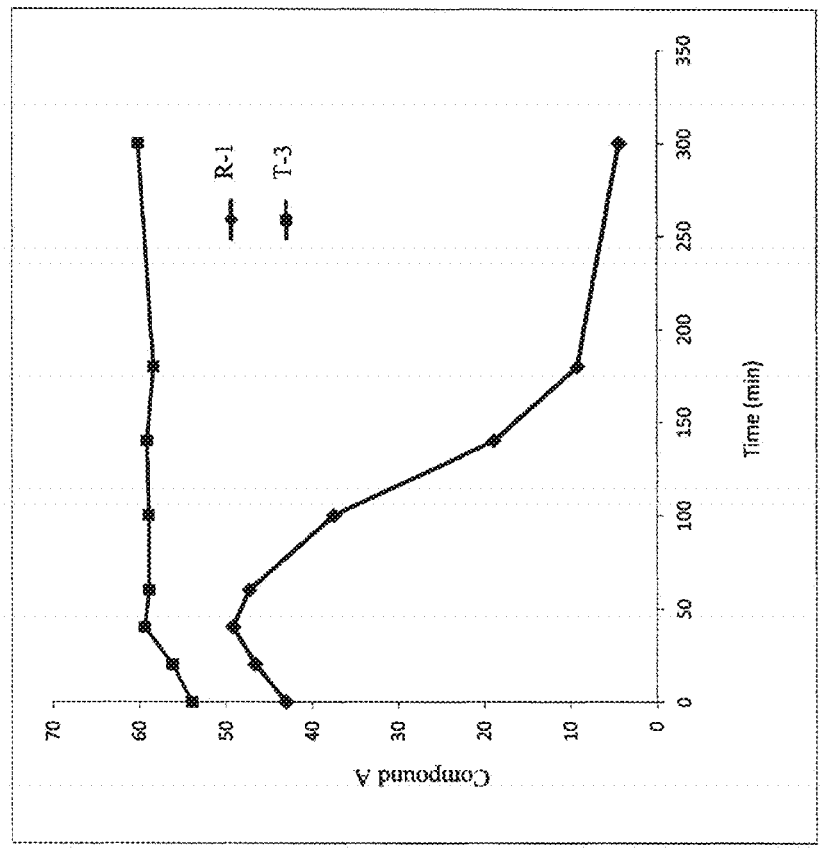
FIG. 10 In vitro pH-dilution dissolution profiles of Formulations R-1 and T-3.

The drug concentration-time profiles measured for Formulation R-1 and Formulation T-3 are shown in FIG. 10. In FIG. 10 the top line corresponds to Formulation T-3 and the bottom line corresponds to Formulation R-1. The drug concentration-time profile for Formulation T-3 shows a stable drug concentration over the duration of the test while the drug concentration-time profile for Formulation R-1 shows a lower drug concentration that continues to decrease over the duration of the test.

Example 6

In Vitro Biphasic Dissolution and In Vivo Dog Studies

Formulations T-3, T-4, and T-5

The three formulations disclosed in Table 14 below were evaluated in an in vitro biphasic dissolution study and also in an in vivo dog study. Formulation T-4 and Formulation T-5 were identical to Formulation T-3 except that the Kollidon VA64 was replaced with an equivalent weight percent of PVP K30 and HPMC-E5, respectively.

TABLE 14

FORMULATIONS T-3, T-4, AND T-5

| COMPONENT | FORMULATION T-3 | FORMULATION T-4 | FORMULATION T-5 |
|---|---|---|---|
| | Compound A monosodium salt monohydrate[a] | | |
| | 250 mg | 250 mg | 250 mg |
| | | % w/w | |
| Compound A monosodium salt monohydrate[a] | 40.0 | 40.0 | 40.0 |
| Microcrystalline Cellulose (Avicel PH 101) | 15.5 | 15.5 | 15.5 |
| Microcrystalline Cellulose (Avicel PH 102) | 15.3 | 15.3 | 15.3 |
| Lactose monohydrate, Fast flo (#316) | 7.0 | 7.0 | 7.0 |
| Kollidon VA64 | 15.0 | — | — |
| PVP K30 | — | 15.0 | — |
| HPMC-E5 | — | — | 15.0 |
| Croscarmellose, Sodium | 5.0 | 5.0 | 5.0 |
| Colloidal Silicon Dioxide | 0.6 | 0.6 | 0.6 |
| Magnesium Stearate | 1.6 | 1.6 | 1.6 |
| Total | 100.0 | 100.0 | 100.0 |

[a]Unit dose and w/w % based on free acid equivalent amount of Compound A.

A. In Vitro Biphasic Dissolution Study

Figure 11:
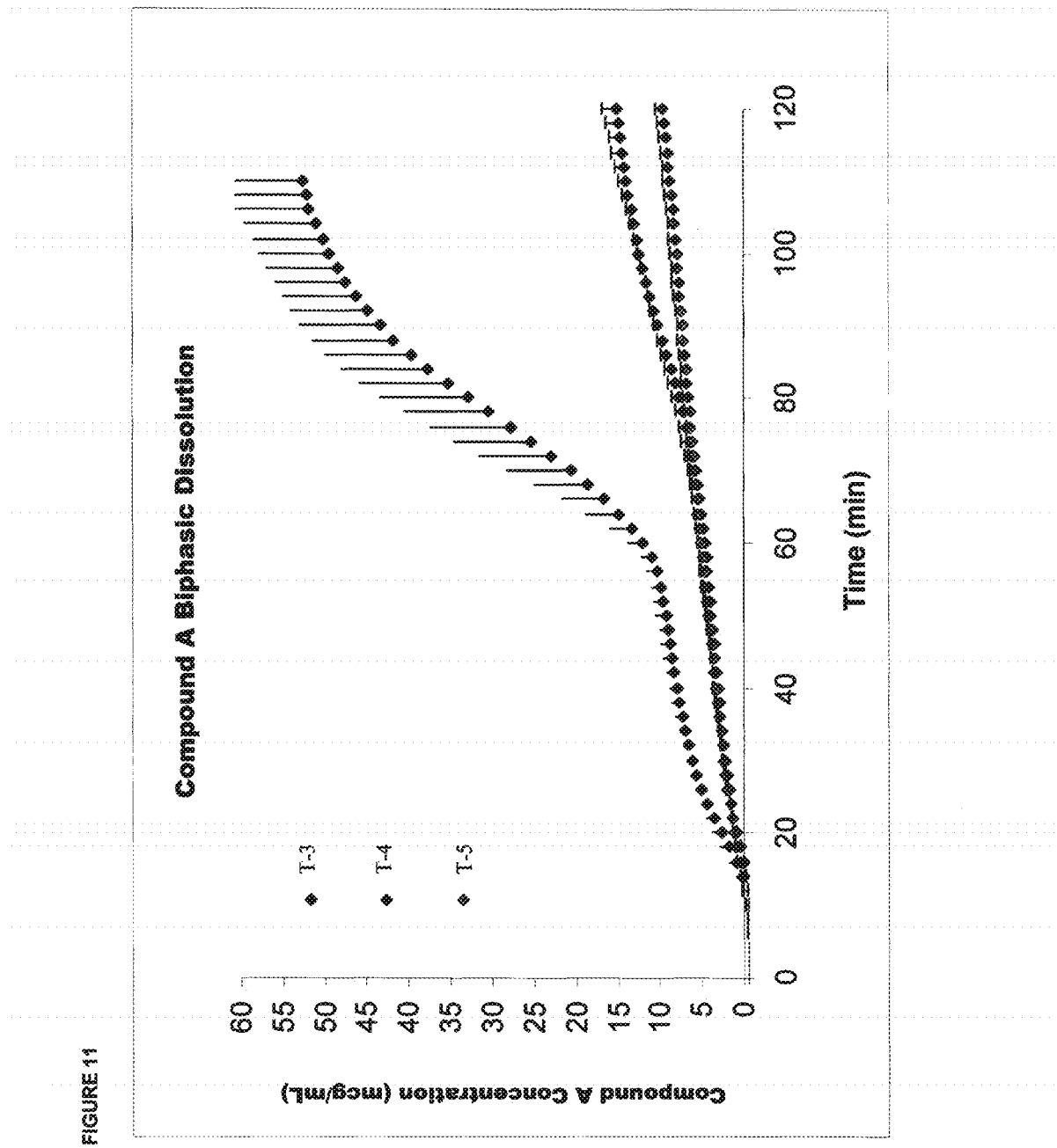
FIG. 11 Biphasic dissolution profiles of Formulations T-3, T-4, and T-5.

An in vitro biphasic dissolution study was conducted with Formulations T-3, T-4, and T-5 to evaluate the effect of different polymers on the oral exposure of Compound A. The study protocol was similar to the protocol of the biphasic dissolution study previously described in Example 2. The in vitro biphasic dissolution profiles for the three formulations are shown in FIG. 11. In FIG. 11 the top line corresponds to Formulation T-3, the middle line corresponds to Formulation T-5, and the bottom line corresponds to Formulation T-4. The data indicate that the Formulations T-4 and T-5 have a lower drug concentration in the octanol phase at the two hour time point than the Formulation T-3.

B. In Vivo Dog Study

An in vivo dog study was conducted with Formulations T-3, T-4, and T-5 to evaluate the effect of different polymers on plasma concentration of Compound A.

The study was a sequential design in a single group of six beagle dogs. The dogs were fasted overnight prior to dosing. Approximately 30 minutes prior to drug administration, each dog received a 100 µg/kg subcutaneous dose of histamine. The dogs received a 250 mg dose of each formulation over five dosing periods. Each tablet was administered orally with 15 mL of chasing water. A washout period of at least one week separated the dosing periods. Blood samples for plasma analysis were obtained from each dog 0.25, 0.5, 1, 1.5, 2, 3, 4, 6, 9, 12, 15 and 24 hours after dosing. Plasma concentrations of Compound A were determined by HPLC-MS/MS.

Figure 12:
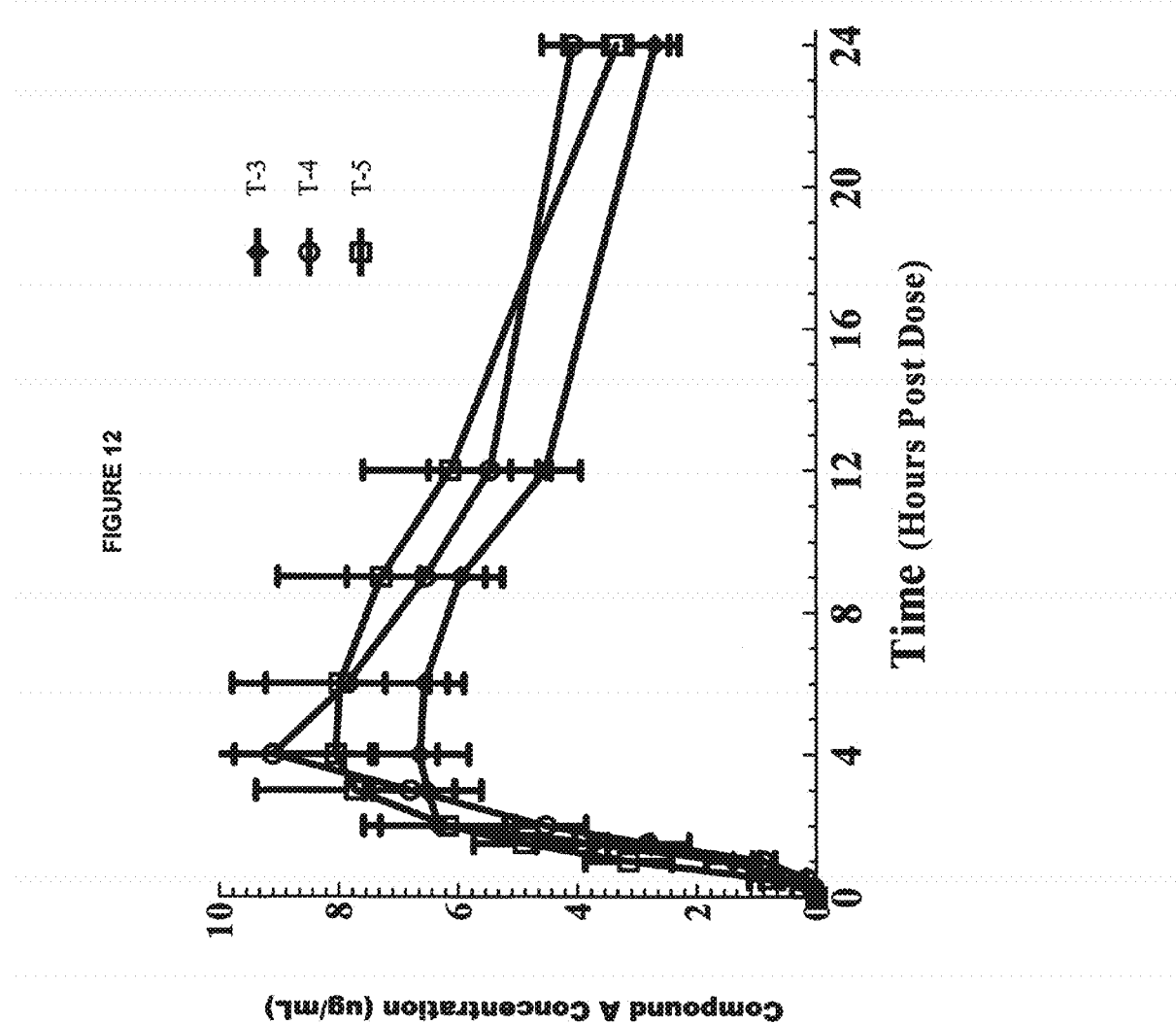
FIG. 12 Pharmacokinetic profiles of Formulations T-3, T-4, and T-5.

Table 15 reports the pharmacokinetic data from the study. Dogs 1 and 3 had frothy emesis at 0.5 hours after being dosed with the Formulation T-5. FIG. 12 shows the mean plasma concentration-time plots for the three formulations.

The data indicate that comparable exposures of Compound A were achieved using three different polymers (Kollidon VA64, PVP K30, and HPMC-E5) at 15% (w/w) and suggest that these three formulations exhibit immediate release and absorption characteristics.

TABLE 15

IN VIVO DOG DATA

| DOG | FORMULATION T-3 | | | FORMULATION T-4 | | | FORMULATION T-5 | | |
|---|---|---|---|---|---|---|---|---|---|
| | $C_{max}$ | $T_{max}$ | $AUC_{0-t}$ | $C_{max}$ | $T_{max}$ | $AUC_{0-t}$ | $C_{max}$ | $T_{max}$ | $AUC_{0-t}$ |
| 1 | 9.96 | 3.0 | 159 | 9.14 | 6.0 | 158 | 13.6 | 6.0 | 236 |
| 2 | 6.72 | 3.0 | 108 | 6.69 | 3.0 | 115 | 7.86 | 4.0 | 132 |
| 3 | 6.87 | 9.0 | 90.5 | 15.0 | 4.0 | 94.8 | 3.71 | 6.0 | 58.7 |
| 4 | 4.85 | 4.0 | 73.4 | 6.25 | 3.0 | 86.4 | 4.80 | 3.0 | 70.3 |
| 5 | 11.1 | 2.0 | 115 | 14.1 | 6.0 | 211 | 14.0 | 3.0 | 225 |
| 6 | 9.06 | 2.0 | 106 | 7.08 | 3.0 | 119 | 6.76 | 4.0 | 99.3 |
| Mean | 8.09 | 3.8 | 109 | 9.71 | 4.2 | 131 | 8.46 | 4.3 | 137 |

° harmonic mean; $C_{max}$ [ug/mL]; $T_{max}$ [hr]; $AUC_{0-t}$ [ug*hr/mL]; V13-1495

Example 7

Enteric Coated Tablet

An enteric coated tablet similar in composition to Formulation T-3 was prepared by coating the Formulation T-3 tablet described in Table 8 with Colorcon's Acryl-EZE White polymer material. The specific composition of the enteric coated tablet is set forth in Table 16 below.

TABLE 16

ENTERIC COATED TABLET (250 mg)

| COMPONENT | AMOUNT |
|---|---|
| Compound A monosodium salt monohydrate | 270.26[a] |
| Microcrystalline Cellulose (Avicel PH 101) | 104.72 |
| Microcrystalline Cellulose (Avicel PH 102) | 103.04 |
| Lactose monohydrate, Fast flo (#316) | 47.30 |
| Kollidon VA64 | 101.35 |
| Croscarmellose, Sodium | 33.78 |
| Colloidal Silicon Dioxide | 4.05 |

TABLE 16-continued

ENTERIC COATED TABLET (250 mg)

| | AMOUNT |
|---|---|
| Magnesium Stearate | 11.15 |
| Opadry II Beige (Film Coating) | 21.00 |
| Tablet Weight | 696.7 |
| ENTERIC COATING | |
| Acryl-EZE White 93O18509 (Colorcon) | 60.60 |
| Purified Water (Processing Aid) | N/A[b] |
| Enteric Coated Tablet Weight | 757.3 |

[a]Equivalent to 250 mg of Compound A (free acid)
[b]Water removed during processing The enteric coated tablet was tested in an in vitro dissolution study and exhibited no release of Compound A in 0.1 N hydrochloric acid over a 120 minute period and more than 90% release of Compound A in a pH 6.8 buffer within 30 minutes. The enteric coated tablet was further evaluated in an in vivo study to determine whether the enteric coating modified and/or delayed the release of Compound A relative to the corresponding tablet without the enteric coating. $T_{max}$ for the enteric coated tablet was delayed relative to the Formulation T-3 tablet, but the $C_{max}$ and $AUC_{24}$ values of the tablets were comparable.

Example 8

Precipitation Inhibition Studies

In vitro crystallization inhibition studies involving Compound A and several different precipitation inhibitors were conducted to evaluate the crystallization properties of Compound A. It is generally believed that crystallization from a meta-stable system (such as a salt or amorphous solid) is governed by two mechanisms. Alonzo, David E., et al., "Understanding the Behavior of Amorphous Pharmaceutical Systems during Dissolution. Pharmaceutical Research," Vol. 27, No. 4, 608-618, April 2010. One mechanism is matrix crystallization where nucleation and crystal growth take place on the surface of the solid before the drug has an opportunity to release into the bulk medium. The second mechanism is solution-mediated crystallization where the molecules (i.e., the salt of Compound A) first dissolve to reach a state of supersaturation which then triggers the crystallization of the stable form (i.e., the free acid of Compound A) resulting in de-supersaturation. Both mechanisms can potentially negate the dissolution advantage of a salt relative to the corresponding free acid. In situations where such crystallization is a potential issue, inhibition of one or both of these crystallization routes can improve the dissolution of the salt.

A. Solid-Based Crystallization Study (Matrix Crystallization)

Several polymers (Kollidon VA64, PVP K30, HPMC E5, HPC SL, Eudragit L-100, HPC SL, SoluPlus, Lutrol F127, and KolliCoat IR) were evaluated for their effectiveness in inhibiting or delaying precipitation of the free acid of Compound A through a solid-based mechanism. In this study the following polymer/buffer solutions were prepared by pre-dissolving the polymer in a pH 6.8 sodium phosphate buffer (50 mM phosphate with ionic strength adjusted to 0.155 M with sodium chloride): 0% (control), 0.05%, 0.1%, and 0.2% (weight polymer/volume buffer). The monosodium monohydrate salt of Compound A was then suspended in each polymer/buffer solution at four different solid-to-liquid ratios (40/1, 20/1, 10/1, and 1/1 mg/mL). The suspensions were agitated at ambient temperature until well-mixed and then stored at ambient temperature for up to eight days. The solid phase of each suspension was monitored by powder x-ray diffraction (PXRD) on Day 1 and through Day 8 where noted in Table 17. The results are reported in Table 17 below.

TABLE 17

| MEDIUM | SOLID/LIQUID RATIO (mg SOLID/mL BUFFER) | FREE ACID DETECTED BY PXRD? | |
|---|---|---|---|
| | | 1 day | 8 days |
| 0.05% Kollidon VA64 | 20/1 | No | No |
| | 10/1 | No | No |
| | 1/1 | No | No |
| 0.1% Kollidon VA64 | 20/1 | No | No |
| | 10/1 | No | No |
| 0.2% Kollidon VA64 | 20/1 | No | No |
| | 10/1 | No | No |
| 0.05% PVP K30 | 20/1 | No | No |
| | 10/1 | No | No |
| | 1/1 | No | No |
| 0.1% PVP K30 | 20/1 | No | No |
| | 10/1 | No | No |
| 0.2% PVP K30 | 20/1 | No | No |
| | 10/1 | No | No |
| 0.05% HPMC E5 | 20/1 | No | No |
| | 10/1 | No | No |
| | 1/1 | No | No |
| 0.1% HPMC E5 | 20/1 | No | No |
| | 10/1 | No | No |
| 0.2% HPMC E5 | 20/1 | No | No |
| | 10/1 | No | No |
| 0.05% Eudragit L-100 | 40/1 | No | No |
| | 1/1 | No | No |
| 0.2% Eudragit L-100 | 40/1 | No | No |
| | 1/1 | No | No |
| 0.05% HPC SL | 40/1 | No | |
| | 1/1 | No | |
| 0.2% HPC SL | 40/1 | No | |
| | 1/1 | No | |
| 0.05% SoluPlus | 40/1 | No | |
| | 1/1 | No | |
| 0.2% SoluPlus | 40/1 | No | |
| | 1/1 | No | |
| 0.05% Lutrol F127 | 40/1 | Yes | |
| | 1/1 | Yes | |
| 0.2% Lutrol F127 | 40/1 | Yes | |
| | 1/1 | Yes | |
| 0.05% KolliCoat IR | 40/1 | Yes | |
| | 1/1 | Yes | |
| 0.2% KolliCoat IR | 40/1 | Yes | |
| | 1/1 | Yes | |

TABLE 17-continued

| MEDIUM | SOLID/LIQUID RATIO (mg SOLID/mL BUFFER) | FREE ACID DETECTED BY PXRD? | |
|---|---|---|---|
| | | 1 day | 8 days |
| pH 6.8 buffer (Control) | 40/1 | Yes | |
| | 20/1 | Yes | |
| | 10/1 | Yes | |
| | 1/1 | Yes | |

The Kollidon VA64, PVP K30, HPMC E5, HPC SL, Eudragit L-100, HPC SL, and SoluPlus, polymers tested reduced the precipitation of the free acid of Compound A in aqueous medium for up to eight days at all solid-to-liquid ratios tested. The Lutrol F127, and KolliCoat IR polymers tested, however, did not reduce precipitation of the free acid of Compound A in aqueous medium.

B. Solution-Based Crystallization Study

Several polymers (Kollidon VA64, HPMC E5, HPMC K3, PVP K30, and Vitamin E TPGS) were evaluated for their effectiveness in inhibiting or delaying precipitation of the free acid of Compound A through a solution-based mechanism. About 0.05 mL of a highly concentrated solution of Compound A monosodium salt monohydrate dissolved in dimethyl sulfoxide (16 mg/mL on a free acid equivalent weight basis) was added to 10 mL of pH 6.8 sodium phosphate buffer (50 mM phosphate with ionic strength adjusted to 0.155 M with sodium chloride) containing one of the polymers at one of three different concentrations (0% (control), 0.001%, 0.01%, and 0.1% (weight polymer/volume buffer %)) to provide a supersaturated Compound A solution (about 80 µg/mL on a free acid equivalent weight basis). The supersaturated solution was continuously stirred at 300 rpm at ambient temperatures (about 26° C.) and the solution concentration was monitored for 30 minutes by an in situ UV/Vis dip probe (µDISS Profiler™, pION Inc, Woburn, Mass. 01801, USA) using an external standard.

The resulting concentration-time profiles for Compound A in 0.001%, 0.01%, and 0.1% polymer/buffer are shown in FIGS. 13-A through 13-F for control (no polymer), Kollidon VA64, HPMC E5, HPMC K3, PVP K30 and Vitamin E TPGS, respectively. In FIGS. 13-A through 13-F the top line corresponds to 0.1% polymer/buffer, the middle line corresponds to 0.01% polymer/buffer, and the bottom line corresponds to 0.001% polymer/buffer. In the absence of polymer (control), the concentration of Compound A in the solution rapidly decreased from about 80 µg/mL to about 20 µg/mL (FIG. 13-A). When polymer was present, however, precipitation of Compound A was delayed up to 30 minutes. In particular, more than 75% of the starting supersaturation concentration was effectively maintained at a polymer concentration of 0.1% (FIGS. 13-B through 13-F).

Example 9

Preparation of Compound a Monosodium Salt Monohydrate

WO2009/039134, which published on Mar. 26, 2009 and is incorporated by reference herein in its entirety, describes the preparation of the pattern B crystal form of the Compound A monosodium salt at page 67, paragraph [328] of the published application.

Example 10

Preparation of Formulation T-3

Figure 14:
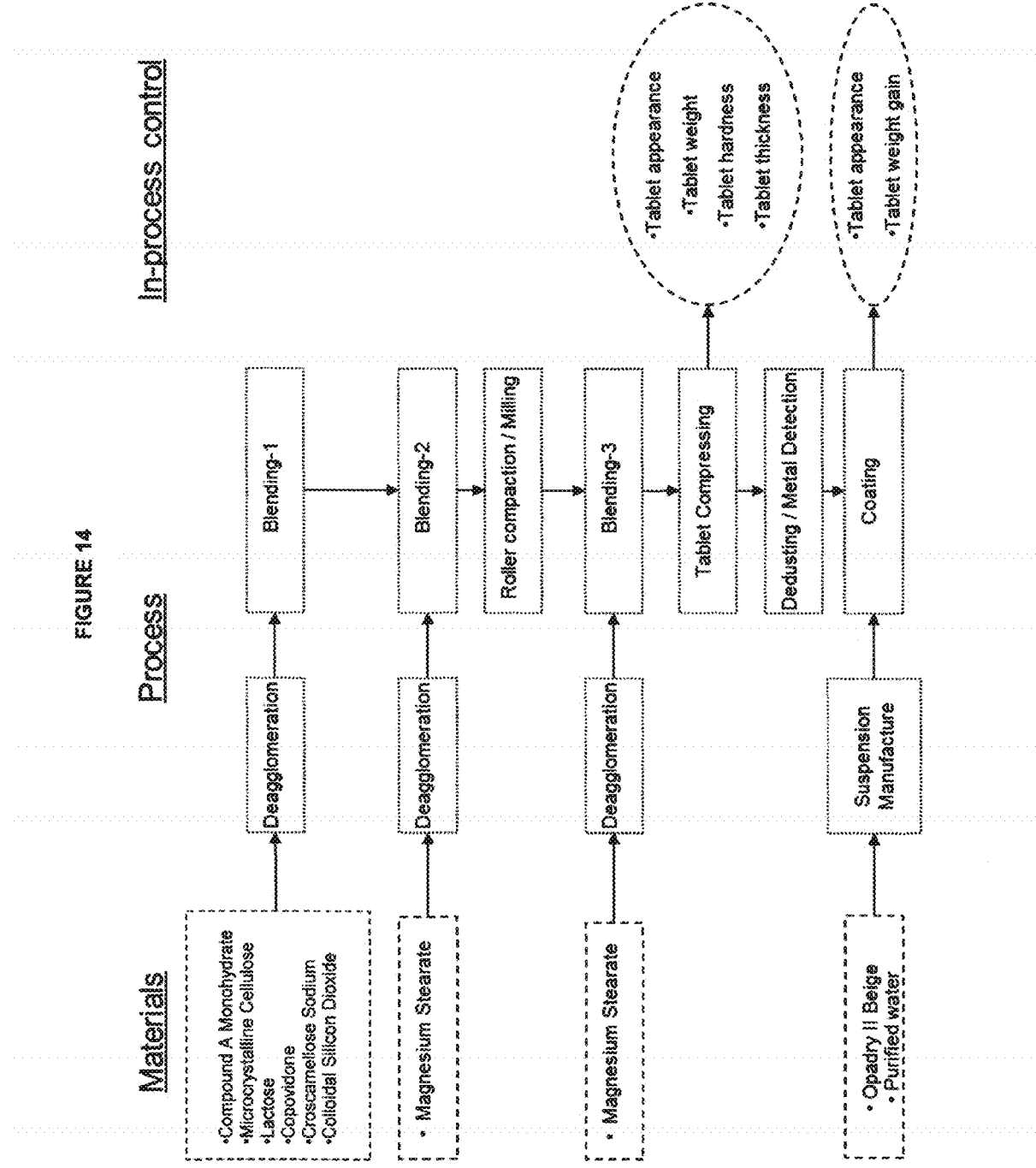
FIG. 14 Manufacturing flow process flow diagram.

Formulation T-3 tablets were prepared as shown in the manufacturing process flow diagram of FIG. 14. The Compound A monosodium salt monohydrate and all excipients except the magnesium stearate were blended together to form a first blend. The first blend was blended with a portion of the magnesium stearate to form a second blend. The second blend was roller compacted using a roller compactor and the ribbons obtained were milled by passing them through a mesh screen with aperture of 1.25 mm coupled with a star-shaped rotor at a speed of 50 rpm. The resulting granules were then further lubricated with the remainder portion of the magnesium stearate and compressed into tablets using a rotary tablet press. The compressed tablets were then coated with Opadry II Beige.

Example 11

Manufacturability

Formulation tabletability was assessed by measuring tablet tensile strength. A formulation with better tabletability will produce stronger tablets with higher tensile strength. In general, to prevent tablet breaking or cracking, higher tablet tensile strength is required for tablet coating and post-manufacturing handling/packaging/shipping processes. The tablet tensile strength was calculated based on tablet hardness, tablet thickness and geometric dimensions of the toolings. Tablet compression was conducted using either a Piccola tablet press or a Korsch tablet press. Tablet compaction characterization was performed using the Presster (Metropolitan Computing Corporation). The tablet breaking force was determined using a Vankel hardness tester. The tablet tensile strength was calculated based on tablet hardness and tablet volume.

The formulations containing 5-25% bioavailability enhancer showed improved tensile strength of the tablets than the formulation without bioavailability enhancer.

The solid fraction of roller compacted ribbons was measured using envelope density meter (GeoPyc 1360). The true density of granules was measured using helium pycnometry (AccuPy1330).

The flowability of formulation granules were assessed using a ring shear cell test. Also tablet weight % rsd were monitored during tablet compression at lab scale or pilot scale for all the formulations listed in Tables 10 and 11. The formulations containing bioavailability enhancers showed improved flowability compared to the formulation without bioavailability enhancer.

In addition, the physical stability of Opadry coated tablets of formulation 10 and Kollicoat IR-coated tablets of formulations 3 and 7 of the sodium salt of compound A prepared by roller compaction was assessed by analytical test and visual observation. The representative stability study on coated tablets for formulation 10 (packaged in HDPE bottle and blister) showed that the tablets remained stable chemically and physically after stored at 40° C./75% RH and 25° C./60% RH for 3 months. In addition, the coated tablets of formulations 3, 7 and 10 were stored at 40° C. at 75% relative humidity in an open dish for 2 to 4 weeks, and remained stable physically and chemically.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A pharmaceutical composition comprising:
   N-(6-(3-tert-butyl-5-(2,4-dioxo-3,4-dihydropyrimidin-1 (2H)-yl)-2-methoxyphenyl)naphthalen-2-yl)methanesulfonamide (Compound A), or a pharmaceutically acceptable salt thereof, in an amount of from about 200 mg to about 300 mg on a free acid equivalent weight basis; and
   a bioavailability enhancing agent which is copovidone in an amount of from about 10% to about 25% by weight of the pharmaceutical composition,
   wherein the solubility of Compound A as measured by a biphasic dissolution test is at least 20 mcg per mL at 100 minutes.

2. The pharmaceutical composition of claim 1, wherein the weight ratio of the bioavailability enhancing agent to Compound A, or the salt thereof, on a free acid equivalent weight basis is from about 4:1 to about 1:8.

3. The pharmaceutical composition of claim 1, wherein the pharmaceutical composition comprises a salt of Compound A.

4. The pharmaceutical composition of claim 3, wherein the salt of Compound A is a sodium salt.

5. The pharmaceutical composition of claim 4, wherein the sodium salt of Compound A is a pattern B crystalline monosodium salt.

6. The pharmaceutical composition of claim 5, wherein the pattern B monosodium salt is a monohydrate.

7. The pharmaceutical composition of claim 1, wherein the amount of Compound A, or salt thereof, is about 250 mg on a free acid equivalent weight basis.

8. The pharmaceutical composition of claim 1, wherein the amount of Compound A, or salt thereof, is at least about 20% by weight of the pharmaceutical composition on a free acid equivalent weight basis.

9. The pharmaceutical composition of claim 1, wherein the bioavailability enhancing agent inhibits precipitation of Compound A, or a salt thereof and wherein the inhibition of precipitation of Compound A, or a salt thereof is determined by the process comprising:
   (i) preparing a test solution comprising Compound A, or a salt thereof, and the bioavailability enhancing agent;
   (ii) preparing a control solution, said control solution being substantially identical to the test solution except that said control solution does not contain the bioavailability enhancing agent;
   (iii) maintaining the test mixture and the control solution under the same conditions for a test period; and
   (iv) determining at the end of the test period the extent to which precipitation of Compound A, or a salt thereof, is inhibited in the test solution relative to the control solution.

10. The pharmaceutical composition of claim 1, wherein the amount of the bioavailability enhancing agent is from about 10% to about 20% by weight of the pharmaceutical composition.

11. The pharmaceutical composition of claim 1, wherein the pharmaceutical composition is an oral dosage form.

12. The pharmaceutical composition of claim 1, wherein the pharmaceutical composition is a tablet.

13. The pharmaceutical composition of claim 11, wherein the oral dosage form has a weight less than about 1500 mg.

14. The pharmaceutical composition of claim 1, wherein the pharmaceutical composition is a tablet having a weight from about 500 mg to about 900 mg.

15. The pharmaceutical composition of claim 12, wherein the tablet when administered as a single dose to a population of human subjects provides an average $AUC_{24}$ value that is at least about 4500 ng·hr/mL for the population of human subjects.

16. The pharmaceutical composition of claim 12, wherein the tablet when administered as a single dose to a population of human subjects provides an average $AUC_{24}$ value that is at least about 5000 ng·hr/mL and an average $C_{max}$ value that is less than about 1200 ng/mL for the population of human subjects.

17. The pharmaceutical composition of claim 1, wherein:
the pharmaceutical composition is an oral dosage form having a weight less than about 1500 mg; and
the oral dosage form comprises Compound A, or a salt thereof, in an amount of about 225 mg to about 275 mg on a free acid equivalent weight basis.

18. The pharmaceutical composition of claim 1, wherein:
the pharmaceutical composition is an oral dosage form having a weight less than about 1500 mg;
the oral dosage form comprises Compound A, or a salt thereof, in an amount of about 240 mg to about 260 mg on a free acid equivalent weight basis.

19. The pharmaceutical composition of claim 1, wherein:
the pharmaceutical composition is an oral dosage form having a weight less than about 1500 mg;
the oral dosage form comprises Compound A, or a salt thereof, in an amount of about 240 mg to about 260 mg on a free acid equivalent weight basis.

20. The pharmaceutical composition of claim 1, wherein:
the pharmaceutical composition is an oral dosage form having a weight less than about 1500 mg;
the oral dosage form comprises Compound A, or a salt thereof, in an amount of about 245 mg to about 255 mg on a free acid equivalent weight basis.

21. The pharmaceutical composition of claim 1, wherein:
the pharmaceutical composition is an oral dosage form having a weight less than about 1500 mg;
the oral dosage form comprises Compound A, or a salt thereof, in an amount of about 240 mg to about 260 mg on a free acid equivalent weight basis; and
the weight ratio of the bioavailability enhancing agent to Compound A, or the salt thereof, on a free acid equivalent weight basis is from about 1:1 to about 1:4.

22. The pharmaceutical composition of claim 1, wherein:
the pharmaceutical composition is an oral dosage form having a weight less than about 1500 mg;
the oral dosage form comprises Compound A, or a salt thereof, in an amount of about 245 mg to about 255 mg on a free acid equivalent weight basis; and
the weight ratio of the bioavailability enhancing agent to Compound A, or the salt thereof, on a free acid equivalent weight basis is from about 1:1 to about 1:4.

23. A method for treating hepatitis C in a subject in need of such treatment, wherein the method comprises administering to the subject a pharmaceutical composition according to claim 1.

24. The method of claim 23 wherein the method further comprises administering to the subject one or more additional therapeutic agents.

25. A method for preparing a pharmaceutical composition according to claim 1, said method comprising blending Compound A, or salt thereof, and the copovidone.

26. A method of enhancing bioavailability of N-(6-(3-tert-butyl-5-(2,4-dioxo-3,4-dihydropyrimidin-1(2H)-yl)-2-methoxyphenyl)naphthalen-2-yl)methanesulfonamide (Compound A), or a pharmaceutically acceptable salt thereof, in a subject comprising: preparing a pharmaceutical composition according to claim 1 and administering the pharmaceutical composition to the subject.

27. A method of improving tabletability of a pharmaceutical composition comprising N-(6-(3-tert-butyl-5-(2,4-dioxo-3,4-dihydropyrimidin-1(2H)-yl)-2-methoxyphenyl) naphthalen-2-yl)methanesulfonamide (Compound A), or a pharmaceutically acceptable salt thereof, said method comprising tableting a pharmaceutical composition according to claim 1 wherein said tablet has improved tensile strength as compared to a similarly tableted pharmaceutical composition not containing copovidone.

28. The pharmaceutical composition of claim 1, wherein the weight ratio of the bioavailability enhancing agent to Compound A, or the salt thereof, on a free acid equivalent weight basis is from 1:1 to 1:3.5.

29. The pharmaceutical composition of claim 12 wherein copovidone is present as an intragranular component.

30. The pharmaceutical composition of claim 1 wherein the solubility of Compound A as measured by a biphasic dissolution test is at least 30 mcg per mL at 100 minutes.

31. The pharmaceutical composition of claim 1 wherein the copovidone concentration is about 15% by weight of the pharmaceutical composition.

32. The pharmaceutical composition of claim 1 wherein the biphasic dissolution test is conducted at a temperature of 37±0.2° C. with an aqueous phase of 40 mL of 80 mM phosphate buffer and an organic phase of 30 mL octanol.

* * * * *

UNITED STATES PATENT AND TRADEMARK OFFICE
CERTIFICATE OF CORRECTION

PATENT NO. : 9,629,841 B2
APPLICATION NO. : 14/058071
DATED : April 25, 2017
INVENTOR(S) : Li et al.

It is certified that error appears in the above-identified patent and that said Letters Patent is hereby corrected as shown below:

On the Title Page

Delete the title page and substitute therefore with the attached title page.

Item (72) Inventor name "Yi Goa" to read as -- Yi Gao --.

The first or sole Notice should read --

Subject to any disclaimer, the term of this patent is extended or adjusted under 35 U.S.C. 154(b) by 9 days.

In the Claims

Column 43, Line 27 - Column 44, Line 49, delete Claims 19-32 and substitute therefore with the following Claims 19-31:

19. The pharmaceutical composition of claim 2, wherein:
    the pharmaceutical composition is an oral dosage form having a weight less than about 1500 mg;
    the oral dosage form comprises Compound A, or a salt thereof, in an amount of about 245 mg to about 255 mg on a free acid equivalent weight basis.

20. The pharmaceutical composition of claim 1, wherein:
    the pharmaceutical composition is an oral dosage form having a weight less than about 1500 mg;
    the oral dosage form comprises Compound A, or a salt thereof, in an amount of about 240 mg to about 260 mg on a free acid equivalent weight basis; and
    the weight ratio of the bioavailability enhancing agent to Compound A, or the salt thereof, on a free acid equivalent weight basis is from about 1:1 to about 1:4.

Signed and Sealed this
Eighteenth Day of September, 2018

Andrei Iancu
*Director of the United States Patent and Trademark Office*

21. The pharmaceutical composition of claim 1, wherein:
   the pharmaceutical composition is an oral dosage form having a weight less than about 1500 mg;
   the oral dosage form comprises Compound A, or a salt thereof, in an amount of about 245 mg to about 255 mg on a free acid equivalent weight basis; and
   the weight ratio of the bioavailability enhancing agent to Compound A, or the salt thereof, on a free acid equivalent weight basis is from about 1:1 to about 1:4.

22. A method for treating hepatitis C in a subject in need of such treatment, wherein the method comprises administering to the subject a pharmaceutical composition according to claim 1.

23. The method of claim 22 wherein the method further comprises administering to the subject one or more additional therapeutic agents.

24. A method for preparing a pharmaceutical composition according to claim 1, said method comprising blending Compound A, or salt thereof, and the copovidone.

25. A method of enhancing bioavailability of $N$-(6-(3-*tert*-butyl-5-(2,4-dioxo-3,4-dihydropyrimidin-1(2$H$)-yl)-2-methoxyphenyl)naphthalen-2-yl)methanesulfonamide (Compound A), or a pharmaceutically acceptable salt thereof, in a subject comprising: preparing a pharmaceutical composition according to claim 1 and administering the pharmaceutical composition to the subject.

26. A method of improving tabletability of a pharmaceutical composition comprising $N$-(6-(3-*tert*-butyl-5-(2,4-dioxo-3,4-dihydropyrimidin-1(2$H$)-yl)-2-methoxyphenyl)naphthalen-2-yl)methanesulfonamide (Compound A), or a pharmaceutically acceptable salt thereof, said method comprising tableting a pharmaceutical composition according to claim 1 wherein said tablet has improved tensile strength as compared to a similarly tableted pharmaceutical composition not containing copovidone.

27. The pharmaceutical composition of claim 1, wherein the weight ratio of the bioavailability enhancing agent to Compound A, or the salt thereof, on a free acid equivalent weight basis is from 1:1 to 1:3.5.

28. The pharmaceutical composition of claim 12 wherein copovidone is present as an intragranular component.

29. The pharmaceutical composition of claim 1 wherein the solubility of Compound A as measured by a biphasic dissolution test is at least 30 mcg per mL at 100 minutes.

30. The pharmaceutical composition of claim 1 wherein the copovidone concentration is about 15% by weight of the pharmaceutical composition.

31. The pharmaceutical composition of claim 1 wherein the biphasic dissolution test is conducted at a temperature of 37 $\pm$ 0.2°C with an aqueous phase of 40 mL of 80 mM phosphate buffer and an organic phase of 30 mL octanol.

CERTIFICATE OF CORRECTION (continued)

(12) United States Patent
Li et al.

(10) Patent No.: US 9,629,841 B2
(45) Date of Patent: Apr. 25, 2017

(54) FORMULATIONS OF PYRIMIDINEDIONE DERIVATIVE COMPOUNDS

(71) Applicant: AbbVie Inc., North Chicago, IL (US)

(72) Inventors: Yanxia Li, Libertyville, IL (US); Ping Gao, Highland Park, IL (US); Yi Shi, Libertyville, IL (US); Geoff G. Zhang, Vernon Hills, IL (US); Yi Gao, Vernon Hills, IL (US); Jianwei Wu, Potomac, MD (US)

(73) Assignee: AbbVie Inc., North Chicago, IL (US)

( * ) Notice: Subject to any disclaimer, the term of this patent is extended or adjusted under 35 U.S.C. 154(b) by 9 days.

(21) Appl. No.: 14/058,071

(22) Filed: Oct. 18, 2013

(65) Prior Publication Data

US 2014/0113921 A1 Apr. 24, 2014

Related U.S. Application Data

(60) Provisional application No. 61/715,766, filed on Oct. 18, 2012.

(51) Int. Cl.
| | |
|---|---|
| *A01N 43/54* | (2006.01) |
| *A61K 31/505* | (2006.01) |
| *A61K 31/513* | (2006.01) |
| *A61K 9/20* | (2006.01) |
| *A61K 9/28* | (2006.01) |

(52) U.S. Cl.
CPC .......... *A61K 31/513* (2013.01); *A61K 9/2027* (2013.01); *A61K 9/2054* (2013.01); *A61K 9/2846* (2013.01); *A61K 9/2866* (2013.01)

(58) Field of Classification Search
CPC .... A61K 31/513; A61K 45/06; A61K 9/2027; A61K 9/2054; A61K 9/2846; A61K 9/2866
See application file for complete search history.

(56) References Cited

U.S. PATENT DOCUMENTS

| | | |
|---|---|---|
| 7,108,864 B1 | 9/2006 | Martino et al. |
| 8,202,912 B2 | 6/2012 | Curatolo et al. |
| 2010/0166861 A1* | 7/2010 | Lynch .......... A61K 9/2027 424/480 |

FOREIGN PATENT DOCUMENTS

| | | |
|---|---|---|
| DE | 4442257 A1 | 5/1996 |
| EP | 2583680 A2 | 4/2013 |
| WO | 2009039127 A1 | 3/2009 |
| WO | 2009039134 A1 | 3/2009 |
| WO | WO 2009039127 A1 * | 3/2009 |
| WO | 2011109274 A1 | 9/2011 |

OTHER PUBLICATIONS

Buhler, Polyvinylpyrrolidone-Excipients for Pharmaceuticals, 2005.*
DiscovIR-LC, Application Note 031, Jul. 2009.*
Jagdale et al, Rev Ciênc Farm Básica Apl., 2010;31(1):25-31.*
Alonzo D.E., et al., "Understanding the Behavior of Amorphous Pharmaceutical Systems During Dissolution," Pharmaceutical Research, 2010, vol. 27 (4), pp. 608-618.
International Search Report and Written Opinion for Application No. PCT/US2013/065760, mailed on Dec. 12, 2013, 13 pages.
Reintjes T., "Solubility Enhancement with BASF Pharma Polymers Solubilizer Compendium", [retrieved on Oct. 1, 2011]. Retrieved from the Internet: < URL: http://www.pharma-ingredients.basf.com /Documents/ENP/Brochure/EN/b_03_110921e_Solubility_Enhance_Compendium.pdf.
Sree Giri P.B., et al: "Formulation and Evaluation of Oro Dispersible Tablets of Stavudine by Direct Compression Technique", [retrived on Jan. 1, 2012], pp. 1505-1514, Retrieved from the Internet: < URL: http://scholarsresearchlibrary.com/dpl-vol4-iss5/ DPL-2912-4-5-1595-1514.pdf.

* cited by examiner

*Primary Examiner* — Jean Cornet

(57) ABSTRACT

The present disclosure relates to pharmaceutical compositions of pyrimidinedione derivative compounds and methods of preparing and uses thereof. The disclosure also relates to methods of enhancing bioavailability of pyrimidinedione derivative compounds in pharmaceutical compositions administered to a subject and methods of reducing the amount of a pyrimidinedione derivative compound in a pharmaceutical composition while achieving the same bioavailability in a subject.

31 Claims, 19 Drawing Sheets